US011925311B2

United States Patent
Endo

(10) Patent No.: US 11,925,311 B2
(45) Date of Patent: Mar. 12, 2024

(54) MEDICAL DIAGNOSIS SUPPORT DEVICE, ENDOSCOPE SYSTEM, AND MEDICAL DIAGNOSIS SUPPORT METHOD

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/944,201

(22) Filed: Sep. 14, 2022

(65) Prior Publication Data

US 2023/0016855 A1 Jan. 19, 2023

Related U.S. Application Data

(63) Continuation of application No. 16/591,585, filed on Oct. 2, 2019, now Pat. No. 11,464,394.

(30) Foreign Application Priority Data

Nov. 2, 2018 (JP) .................................. 2018-207122

(51) Int. Cl.
*A61B 1/00* (2006.01)
*A61B 1/06* (2006.01)
*G06V 10/25* (2022.01)
*G06V 10/764* (2022.01)
*G06V 10/82* (2022.01)

(52) U.S. Cl.
CPC .... *A61B 1/000094* (2022.02); *A61B 1/00006* (2013.01); *A61B 1/000096* (2022.02); *A61B 1/0005* (2013.01); *A61B 1/0638* (2013.01); *G06V 10/25* (2022.01); *G06V 10/764* (2022.01); *G06V 10/82* (2022.01); *G06V 2201/03* (2022.01)

(58) Field of Classification Search
None
See application file for complete search history.

(56) References Cited

U.S. PATENT DOCUMENTS 10,863,893 B2 * 12/2020 Imaizumi .............. G06T 7/0012
2011/0254937 A1 * 10/2011 Yoshino ............... A61B 1/0655
348/E7.085

(Continued)

*Primary Examiner* — John P Leubecker
*Assistant Examiner* — Jae Woo
(74) *Attorney, Agent, or Firm* — JCIPRNET

(57) ABSTRACT

An object of the invention is to provide a medical diagnosis support device, an endoscope system, and a medical diagnosis support method where the visibility of a recognition result of a medical image is high.

A medical diagnosis support device according to an aspect of the invention includes an image acquisition section that acquires medical images in time series, a detection section that detects a region of interest included in the medical images, a discrimination section that performs the discrimination of the medical images, a display control section that causes a display device to display any one of a result of the detection or a result of the discrimination, and a setting section that sets a waiting time required until the display is performed after the detection or the discrimination is performed. In a case where an object to be displayed is switched between the result of the detection and the result of the discrimination, the display control section causes the result of the detection or the discrimination to be displayed when the waiting time has passed after the detection or the discrimination is performed.

23 Claims, 17 Drawing Sheets

(56) References Cited

U.S. PATENT DOCUMENTS

| | | | |
|---|---|---|---|
| 2012/0035507 A1* | 2/2012 | George | A61B 1/00097 |
| | | | 600/587 |
| 2012/0274754 A1* | 11/2012 | Tsuruoka | A61B 1/0638 |
| | | | 348/222.1 |
| 2018/0242817 A1* | 8/2018 | Imaizumi | G06T 11/60 |
| 2018/0249900 A1* | 9/2018 | Imaizumi | G02B 23/2484 |
| 2019/0050681 A1* | 2/2019 | Tate | G06F 18/24 |
| 2020/0046208 A1* | 2/2020 | Kasai | A61B 1/3132 |
| 2020/0065989 A1* | 2/2020 | Bai | G06T 7/11 |

* cited by examiner

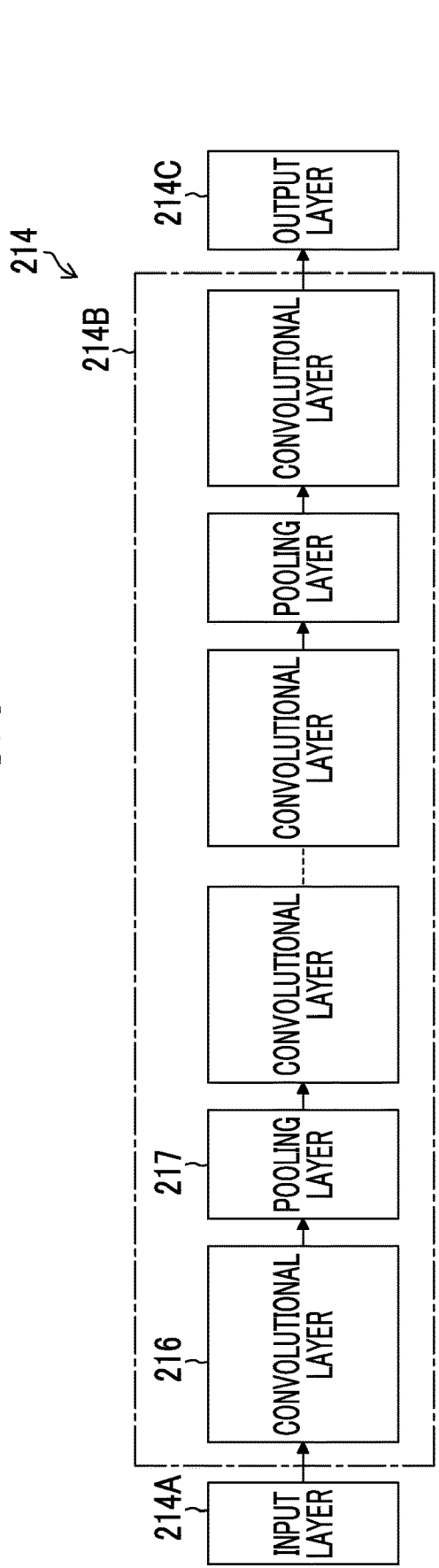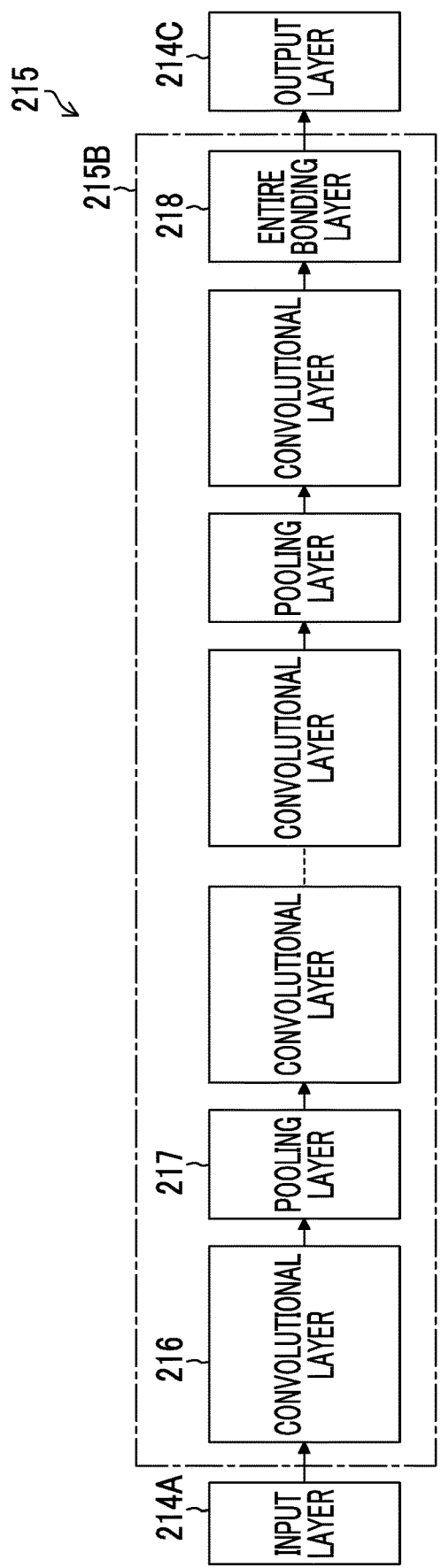
FIG. 6A
FIG. 6B

MEDICAL DIAGNOSIS SUPPORT DEVICE, ENDOSCOPE SYSTEM, AND MEDICAL DIAGNOSIS SUPPORT METHOD

CROSS-REFERENCE TO RELATED APPLICATIONS

This application is a continuation application of and claims priority benefit of a prior application Ser. No. 16/591,585, filed on Oct. 2, 2019, now allowed. The prior application Ser. No. 16/591,585 claims priority under 35 U.S.C. § 119 to Japanese Patent Application No. 2018-207122, filed on Nov. 2, 2018. The entirety of each of the above applications is hereby expressly incorporated by reference, in its entirety, into the present application.

BACKGROUND OF THE INVENTION

1. Field of the Invention

The present invention relates to a medical diagnosis support device, an endoscope system, and a medical diagnosis support method that perform the recognition of a medical image and display the result thereof.

2. Description of the Related Art

In diagnosis support using a medical image, there is a case where the recognition of an image is performed and the result thereof is displayed on a display device. For example, a recognition result is displayed through the emphasis display of a region of interest detected from an image, but a technique for delaying a timing where such a display is performed is known. For example, WO17/203560A discloses an endoscopic image processing device that performs emphasis processing on an image to be input when a first time has passed from a timing where the detection of a region of interest is started.

SUMMARY OF THE INVENTION

In observation or diagnosis that is performed by medical equipment, such as an endoscope, there is a case where the contents (the detection of a region of interest, the discrimination of an image, or the like) to be recognized from an acquired medical image or an object to be displayed (the type of recognition of which the result is to be displayed, or the like) is switched. However, since emphasis display in a case where a region of interest is detected is merely delayed on the basis of (at least one of) the position information and size information of the region of interest in WO17/203560A, the switching of an object to be recognized or an object to be displayed is not considered. Accordingly, for example, in a case where another recognition is performed after certain recognition and processing then returns to the initial recognition, the recognition result of the same subject (a region of interest or the like) is displayed immediately after the switching of recognition. For this reason, there is a concern that a user may feel inconvenient and observation or diagnosis may be hindered. As described above, visibility in a case where an object to be recognized or an object to be displayed is switched is not considered in the related art.

The invention has been made in consideration of the above-mentioned circumstances, and an object of the invention is to provide a medical diagnosis support device, an endoscope system, and a medical diagnosis support method where the visibility of a recognition result of a medical image is high.

In order to achieve the above-mentioned object, a medical diagnosis support device according to a first aspect of the invention comprises an image acquisition section that acquires medical images in time series, a detection section that detects a region of interest included in the medical images, a discrimination section that performs discrimination of the medical images, a display control section that causes a display device to display any one of a result of the detection or a result of the discrimination, and a setting section that sets a waiting time required until the display is performed after the detection or the discrimination is performed. In a case where an object to be displayed is switched between the result of the detection and the result of the discrimination, the display control section causes the result of the detection or the discrimination to be displayed when the waiting time has passed after the detection or the discrimination is performed. In the first aspect, in a case where an object to be displayed is switched between the result of the detection and the result of the discrimination, the result of the detection or the discrimination is caused to be displayed when the waiting time has passed after the detection or the discrimination is performed. Accordingly, since a recognition result about the same subject (a region of interest or the like) is not displayed immediately after switching, a user does not feel inconvenient and observation or diagnosis is not hindered. As a result, the visibility of the recognition result of the medical image is high.

In the first aspect, one of the detection and the discrimination may be performed by the switching and the result thereof may be displayed, or both of recognition may be performed in parallel and an object to be displayed (the result of the detection or the result of the discrimination) may be switched. That is, an object to be displayed may be switched by the switching of the recognition, or an object to be displayed may be switched without switching the recognition. The result of the detection can be displayed by the superimposition and display of figures or symbols, the display of position coordinates with numerical values, a change in the color or gradation of the region of interest, or the like according to a position where the region of interest is detected, the size or shape of the region of interest, or the like; and the result of the discrimination can be displayed with characters, numbers, figures, symbols, colors, and the like. The result of the detection and the result of the discrimination may be superimposed and displayed on the medical image, and may be displayed separately from the image (displayed in a separate region of a display screen, displayed on a separate screen, or the like). The discrimination can be performed for all or some of the medical images regardless of the result of the detection.

In the first aspect, the medical image may be picked up and acquired at the time of the recognition or an image picked up in advance may be acquired as the medical image. That is, the acquisition, recognition, and display of the image may be performed in parallel, or an image, which is picked up in advance and recorded, may be recognized and displayed after the fact. Further, the medical image, which is acquired by the image acquisition section, may be an image that is obtained by performing image processing (the emphasis of a specific subject or a specific color component (frequency band), or the like) on a picked-up image. The medical diagnosis support device according to the first aspect can be realized as, for example, a processor of an image diagnosis support system or an endoscope system or a computer for processing a medical image, but is not limited thereto.

"Acquires medical images in time series" in the first aspect includes, for example, a case where medical images corresponding to a plurality of frames are acquired with a determined frame rate. The medical diagnosis support device according to the first aspect may comprise a repetition control section that continues processing (detecting, discriminating, and displaying) the medical images until an end condition is satisfied. Further, in the first aspect and the respective aspects to be described below, a "region of interest" (ROI) is referred to as a "region of concern". Furthermore, in the first aspect and the respective aspects to be described below, a medical image is referred to as an image for medical use.

According to a second aspect, the medical diagnosis support device according to the first aspect further comprises an estimation section that estimates the amount of movement between frames of the medical images, and the setting section sets the waiting time according to the estimated amount of movement.

According to a third aspect, in the medical diagnosis support device according to the second aspect, in a case where the amount of movement is larger than a threshold value, the setting section sets a waiting time, which is shorter than a waiting time corresponding to the threshold value, as the waiting time. Further, in a case where the amount of movement is equal to or smaller than the threshold value, the setting section sets a waiting time, which is longer than a waiting time corresponding to the threshold value, as the waiting time. The third aspect is to shorten the waiting time since a different subject (a region of interest or the like) is likely to be seen in a case where the amount of movement is large and to lengthen the waiting time since the same subject is likely to be seen in a case where the amount of movement is small (In this case, there is a concern that diagnosis may be hindered since a user feels inconvenient in a case where a result is instantly displayed).

According to a fourth aspect, the medical diagnosis support device according to any one of the first to third aspects further comprises a storage control section that stores information about the region of interest, which is detected from the medical images, in a storage device, and a determination section that determines whether or not the region of interest detected by the detection section is a region of interest having been already detected on the basis of the stored information. Further, in a case where it is determined that the region of interest detected by the detection section is a region of interest having been already detected, the display control section does not perform the display even though the waiting time has passed. There is a possibility that a user feels inconvenient in a case where the result of the region of interest having been already detected is repeatedly displayed. Accordingly, in the fourth aspect, display is not performed even though the waiting time has passed in such a case.

According to a fifth aspect, the medical diagnosis support device according to any one of the first to fourth aspects further comprises a receiving section that receives a user's operation, and the setting section sets the waiting time on the basis of the received operation. According to the fifth aspect, a user (a doctor or the like) can input a desired value.

According to a sixth aspect, in the medical diagnosis support device according to the fifth aspect, the setting section sets a waiting time, which is selected from a plurality of predetermined waiting times by the user's operation, as the waiting time. According to the sixth aspect, a user can easily set the waiting time.

According to a seventh aspect, in the medical diagnosis support device according to any one of the first to sixth aspects, until the waiting time has passed, the display control section causes the display device to display information representing that the result of the detection or the result of the discrimination is not displayed. In a case where the result is not displayed, there is a possibility that a user is anxious about whether or not the device operates correctly. However, in a case where the information is displayed as in the seventh aspect, such an anxiety can be eliminated.

According to an eighth aspect, in the medical diagnosis support device according to any one of the first to seventh aspects, the setting section sets a first waiting time, which is a waiting time required in a case where the object to be displayed is switched to the result of the detection from the result of the discrimination, as the waiting time. Further, in a case where the object to be displayed is switched to the result of the detection from the result of the discrimination, the display control section causes the result of the detection to be displayed when the first waiting time has passed after the detection is performed. The setting section may set the first waiting time according to a user's operation, or may set the first waiting time regardless of a user's operation.

According to a ninth aspect, in the medical diagnosis support device according to any one of the first to eighth aspects, the setting section sets a second waiting time, which is a waiting time required in a case where the object to be displayed is switched to the result of the discrimination from the result of the detection, as the waiting time. Further, in a case where the object to be displayed is switched to the result of the discrimination from the result of the detection, the display control section causes the result of the discrimination to be displayed when the second waiting time has passed after the discrimination is performed. The setting section may set the second waiting time according to a user's operation, or may set the second waiting time regardless of a user's operation.

According to a tenth aspect, the medical diagnosis support device according to any one of the first to ninth aspects further comprises an operation control section that operates any one of the detection section or the discrimination section. Further, in a case where the object to be operated is switched between the detection section and the discrimination section, the display control section determines that the object to be displayed is switched between the result of detection and the result of discrimination and causes the result of detection or the result of the discrimination, which is obtained from the operation, to be displayed. Accordingly, a user does not need to switch an object to be displayed, separately from the switching of an object to be operated. The operation control section may determine which one of the detection section and the discrimination section is to be operated according to a user's operation.

According to an eleventh aspect, in the medical diagnosis support device according to any one of the first to ninth aspects, the detection performed by the detection section and the discrimination performed by the discrimination section are performed in parallel. Accordingly, the result of the detection and the result of the discrimination are obtained, but the display control section displays the result of the detection or the result of the discrimination by the switching of an object to be displayed. "Performed in parallel"

includes a case where both the detection and the discrimination are performed for frames of the medical images acquired in time series.

According to a twelfth aspect, in the medical diagnosis support device according to any one of the first to eleventh aspects, the detection section performs the detection by using a first hierarchical network and the discrimination section performs the discrimination by using a second hierarchical network. The twelfth aspect is to prescribe one aspect of the configuration of each of the detection section and the discrimination section. For example, a Convolutional Neural Network (CNN) formed by machine learning, such as deep learning, can be used as the hierarchical network.

In order to achieve the above-mentioned object, an endoscope system according to a thirteenth aspect of the invention comprises the medical diagnosis support device according to any one of the first to twelfth aspects, the display device, an endoscope that is to be inserted into an object to be examined, and a light source device that applies one of first illumination light and second illumination light different from the first illumination light to the object to be examined. According to the thirteenth aspect, since the detection and the discrimination can be performed by the medical diagnosis support device according to any one of the first to twelfth aspects and the results thereof can be displayed, the visibility of the recognition result of the medical image is high.

In the thirteenth aspect, the first illumination light and the second illumination light may be normal light and special light (narrow-band light or the like) or may be first special light and second special light. Further, it can be determined that, for example, a case where at least one of a wavelength range or a spectrum is not identical corresponds to "illumination light is different". A light source device, which can apply other illumination light (third illumination light, fourth illumination light, and the like) in addition to the first illumination light and the second illumination light, may be used.

In the thirteenth aspect, light emitted from a light source may be used as illumination light just as it is, or light generated through the application of a filter, which transmits light in a specific wavelength range, to light emitted from a light source may be used as the illumination light. For example, in a case where narrow-band light is used as the illumination light, light applied from a light source for narrow-band light may be used as the illumination light or light generated through the application of a filter, which transmits light in a specific wavelength range, to white light may be used as the illumination light. In this case, filters to be applied to white light may be sequentially switched to apply different kinds of narrow-band light at different timings.

According to a fourteenth aspect, in the endoscope system according to the thirteenth aspect, the light source device switches the first illumination light and the second illumination light while interlocking with the switching of the detection and the discrimination. According to the fourteenth aspect, a user does not need to perform an operation for switching illumination light, separately from the switching of the recognition.

According to a fifteenth aspect, in the endoscope system according to the thirteenth aspect, the light source device switches the first illumination light and the second illumination light independently of the switching of the detection and the discrimination. The switching of the illumination light can be performed according to a user's operation. Accordingly, a user can perform the recognition (the detection or the discrimination) with desired illumination light. The illumination light at the time of the detection and the illumination light at the time of the discrimination may be same or may be different from each other.

In order to achieve the above-mentioned object, a medical diagnosis support method according to a sixteenth aspect of the invention comprises an image acquisition step of acquiring medical images in time series, a detection step of detecting a region of interest included in the medical images, a discrimination step of performing discrimination of the medical images, a display control step of causing a display device to display any one of a result of the detection or a result of the discrimination, and a setting step of setting a waiting time required until the display is performed after the detection or the discrimination is performed. In a case where an object to be displayed is switched between the result of the detection and the result of the discrimination, the result of the detection or the discrimination is caused to be displayed in the display control step when the waiting time has passed after the detection or the discrimination is performed. In the medical diagnosis support method according to the sixteenth aspect, the visibility of the recognition result of the medical image is high as in the first aspect.

The medical diagnosis support method according to the sixteenth aspect may further include the same configuration as the second to twelfth aspects. Further, examples of an aspect of the invention can also include a program that causes the medical image processing device or the endoscope system to perform the medical diagnosis support methods according to these aspects and a non-temporary recording medium in which computer-readable codes of the program are recorded.

As described above, the visibility of the recognition result of the medical image is high in the medical diagnosis support device, the endoscope system, and the medical diagnosis support method according to aspects of the invention.

BRIEF DESCRIPTION OF THE DRAWINGS

FIGS. 6A and 6B are diagrams showing an example of the configuration of a convolutional neural network.

DESCRIPTION OF THE PREFERRED EMBODIMENTS

A medical diagnosis support device, an endoscope system, and a medical diagnosis support method according to embodiments of the invention will be described in detail below with reference to the accompanying drawings.

First Embodiment

Figure 1:
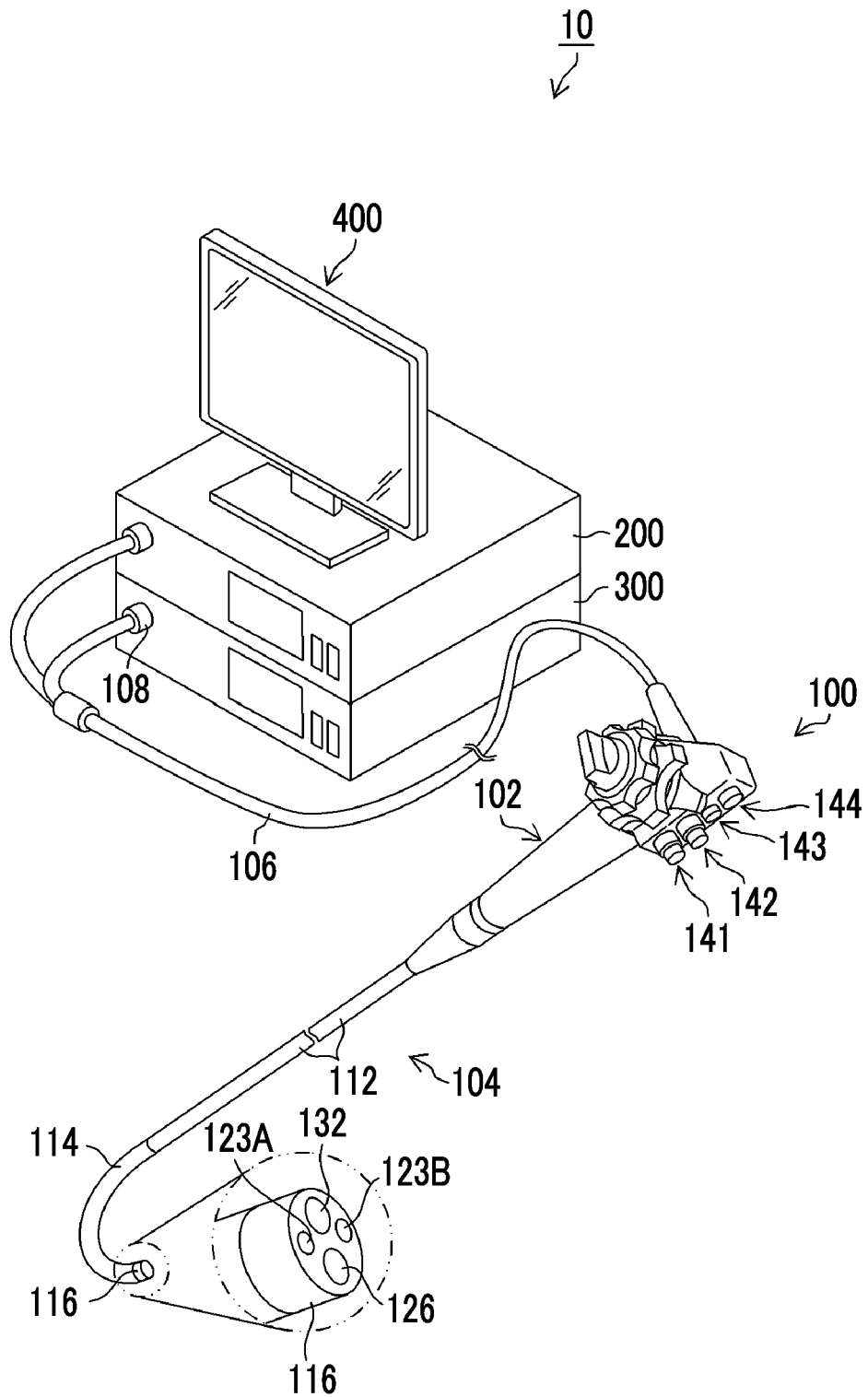
FIG. 1 is a diagram showing the appearance of an endoscope system according to a first embodiment.
Figure 2:
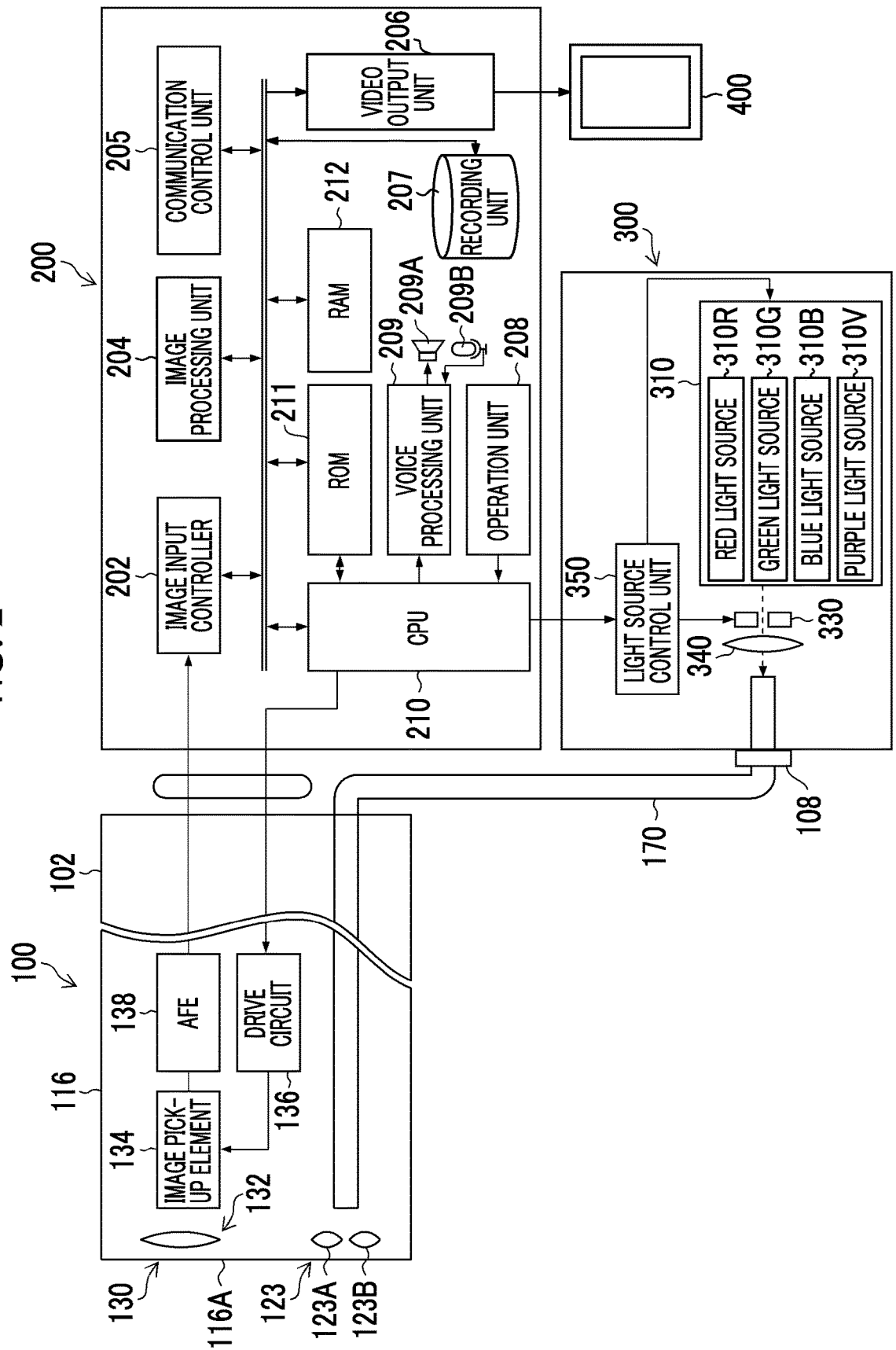
FIG. 2 is a block diagram showing the configuration of the endoscope system.

FIG. 1 is a diagram showing the appearance of an endoscope system 10 (a medical-use image processing device, a medical image processing device, a medical diagnosis support device, an endoscope system) according to a first embodiment, and FIG. 2 is a block diagram showing the main configuration of the endoscope system 10. As shown in FIGS. 1 and 2, the endoscope system 10 includes an endoscope 100 (an endoscope, an endoscope body), a processor 200 (a processor, an image processing device, a medical image processing device, a medical diagnosis support device), a light source device 300 (light source device), and a monitor 400 (display device).

Configuration of Endoscope

The endoscope 100 comprises a hand operation part 102 (hand operation part) and an insertion part 104 (an insertion part) connected to the hand operation part 102. An operator (user) grips and operates the hand operation part 102, inserts the insertion part 104 into an object to be examined (living body), and observes the object to be examined. Further, the hand operation part 102 is provided with an air/water supply button 141, a suction button 142, a function button 143 to which various functions are assigned, and an image pick-up button 144 that receives an instruction operation (a static image or a video) for starting and ending image pick-up. Functions, such as the switching of contents to be recognized (detection, discrimination, and the like to be described later), the setting or switching of an object to be displayed, and the switching of illumination light, may be assigned to the function button 143. The insertion part 104 includes a soft portion 112 (soft portion), a bendable portion 114 (bendable portion), and a hard distal end portion 116 (hard distal end portion) that are arranged in this order from the hand operation part 102. That is, the bendable portion 114 is connected to the proximal end side of the hard distal end portion 116, and the soft portion 112 is connected to the proximal end side of the bendable portion 114. The hand operation part 102 is connected to the proximal end side of the insertion part 104. In a case where a user operates the hand operation part 102, the user can bend the bendable portion 114 to vertically and laterally change the direction of the hard distal end portion 116. The hard distal end portion 116 is provided with an image pick-up optical system 130 (an image pick-up unit), an illumination unit 123, a forceps port 126, and the like (see FIGS. 1 to 3).

At the time of observation and treatment, narrow-band light (one or more of red narrow-band light, green narrow-band light, blue narrow-band light, and purple narrow-band light) as white light and/or special light can be applied from illumination lenses 123A and 123B of the illumination unit 123 by the operation of an operation unit 208 (see FIG. 2). Further, cleaning water is ejected from a water supply nozzle (not shown) by the operation of the air/water supply button 141, so that an image pick-up lens 132 (an image pick-up lens or an image pick-up unit) of the image pick-up optical system 130 and the illumination lenses 123A and 123B can be cleaned. A pipe line (not shown) communicates with the forceps port 126 that is opened to the hard distal end portion 116, and a treatment tool (not shown) for the removal of a tumor or the like is inserted into the pipe line and is appropriately moved back and forth to perform necessary treatment on an object to be examined.

Figure 3:
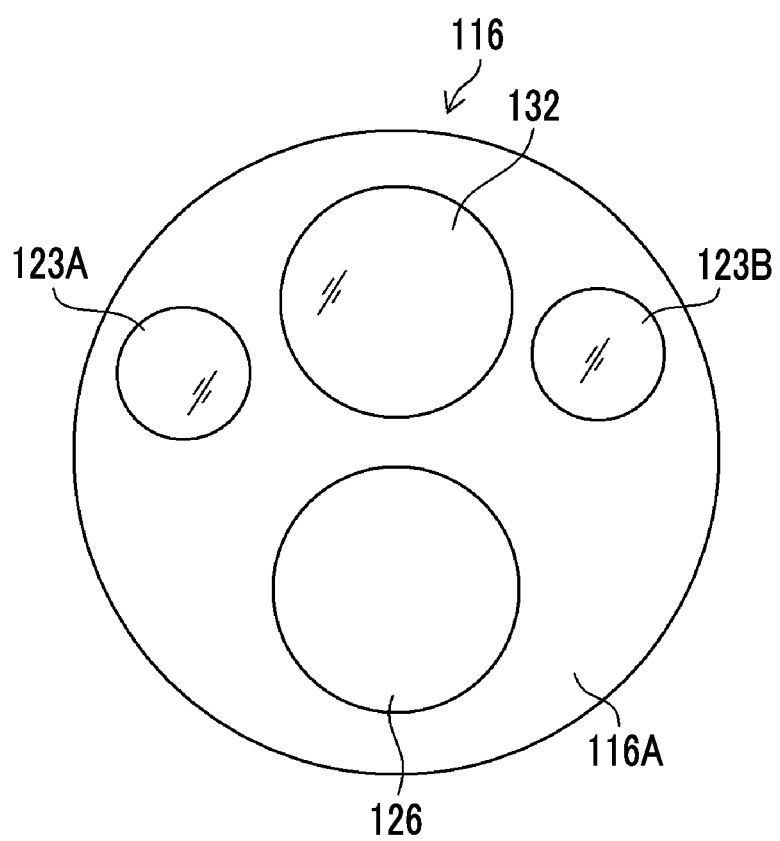
FIG. 3 is a diagram showing the configuration of a hard distal end portion of an endoscope.

As shown in FIGS. 1 to 3, the image pick-up lens 132 (the image pick-up unit) is provided on a distal end-side end face 116A of the hard distal end portion 116. A complementary-metal-oxide-semiconductor (CMOS) type image pick-up element 134 (an image pick-up element or an image pick-up unit), a drive circuit 136, and an analog front end (AFE) 138 are provided in the back of the image pick-up lens 132, and image signals are output by these elements. The image pick-up element 134 is a color image pick-up element, and comprises a plurality of pixels formed of a plurality of light-receiving elements that are arranged in the form of a matrix (two-dimensionally arrayed) so as to have a specific pattern array (a Bayer array, an X-Trans (registered trademark) array, a honeycomb array, or the like). Each pixel of the image pick-up element 134 includes a microlens, a red (R), green (G), or blue (B) color filter, and a photoelectric conversion part (a photodiode or the like). The image pick-up optical system 130 also can generate a color image from pixel signals corresponding to three colors of red, green, and blue, and also can generate an image from pixel signals corresponding to any one color or two colors of red, green, and blue. A case where the image pick-up element 134 is a CMOS type image pick-up element has been described in the first embodiment, but the image pick-up element 134 may be a charge-coupled-device (CCD) type image pick-up element. Each pixel of the image pick-up element 134 may further comprise a purple color filter corresponding to a purple light source and/or an infrared filter corresponding to an infrared light source. In this case, an image can be generated in consideration of ultraviolet and/or infrared pixel signals.

The optical image of an object to be examined (a tumor area or a lesion area) is formed on the light-receiving surface (image pick-up surface) of the image pick-up element 134 by the image pick-up lens 132 and is converted into electrical signals, and the electrical signals are output to the processor 200 through a signal cable (not shown) and are converted into video signals. Accordingly, an observation image is displayed on the monitor 400 connected to the processor 200.

Further, the illumination lenses 123A and 123B of the illumination unit 123 are provided on the distal end-side end face 116A of the hard distal end portion 116 so as to be adjacent to the image pick-up lens 132. An emitting end of a light guide 170 to be described later is provided in the back of the illumination lenses 123A and 123B; the light guide 170 is inserted into the insertion part 104, the hand operation part 102, and the universal cable 106; and an incident end of the light guide 170 is disposed in a light guide connector 108.

Configuration of Light Source Device

As shown in FIG. 2, the light source device 300 includes a light source 310 for illumination, a stop 330, a condenser lens 340, a light source control unit 350, and the like, and causes illumination light (observation light) to be incident on the light guide 170. Since the light source 310 comprise a red light source 310R, a green light source 310G, a blue light source 310B, and a purple light source 310V that apply red narrow-band light, green narrow-band light, blue narrow-band light, and purple narrow-band light, respectively, the light source 310 can apply red narrow-band light, green narrow-band light, blue narrow-band light, and purple narrow-band light. The illuminance of illumination light applied by the light source 310 is controlled by the light source control unit 350, so that the illuminance of illumination light can be lowered and illumination can be stopped as necessary.

The light source 310 can emit light while randomly combining red narrow-band light, green narrow-band light, blue narrow-band light, and purple narrow-band light. For example, the light source 310 can also apply white light (normal light; an example of first illumination light) as illumination light (observation light) by simultaneously emitting red narrow-band light, green narrow-band light, blue narrow-band light, and purple narrow-band light; and can also apply narrow-band light (an example of second illumination light) as special light by emitting any one or two of red narrow-band light, green narrow-band light, blue narrow-band light, and purple narrow-band light. The light source 310 may further comprise an infrared light source that applies infrared light (an example of narrow-band light). Further, the light source 310 may apply white light or narrow-band light as illumination light by a light source applying white light and a filter transmitting white light and each narrow-band light. By the control of the light source control unit 350, the light source device 300 can also switch the first illumination light and the second illumination light while interlocking with the switching of detection and discrimination to be described later and can also switch the first illumination light and the second illumination light independently of the switching of detection and discrimination. In a case where the light source device 300 switches the first illumination light and the second illumination light while interlocking with the switching of detection and discrimination, a user does not need to perform an operation for switching illumination light separately from the switching of recognition. In a case where the light source device 300 switches the first illumination light and the second illumination light independently of the switching of detection and discrimination, a user can perform recognition (detection or discrimination) by desired illumination light. The switching of illumination light may be performed according to a user's operation that is performed through the operation unit 208 and the function button 143, and may also be performed regardless of a user's operation.

Wavelength Range of Light Source

The light source 310 may be a light source that generates light in a white-light wavelength range or generates light in a plurality of wavelength ranges as light in a white-light wavelength range, and may be a light source that generates light in a specific wavelength range narrower than the white-light wavelength range. The specific wavelength range may be a blue-light wavelength range or a green-light wavelength range of a visible-light wavelength range or a red-light wavelength range of a visible-light wavelength range. In a case where the specific wavelength range is a blue-light wavelength range or a green-light wavelength range of a visible-light wavelength range, the specific wavelength range may include a wavelength range of 390 nm to 450 nm or 530 nm to 550 nm and light in the specific wavelength range may have a peak wavelength in a wavelength range of 390 nm to 450 nm or 530 nm to 550 nm. Further, in a case where the specific wavelength range is a red-light wavelength range of a visible-light wavelength range, the specific wavelength range may include a wavelength range of 585 nm to 615 nm or 610 nm to 730 nm and light in the specific wavelength range may have a peak wavelength in a wavelength range of 585 nm to 615 nm or 610 nm to 730 nm.

Light in the above-mentioned specific wavelength range may include a wavelength range where a light absorption coefficient in oxyhemoglobin is different from that in reduced hemoglobin, and may have a peak wavelength in a wavelength range where a light absorption coefficient in oxyhemoglobin is different from that in reduced hemoglobin. In this case, the specific wavelength range may include a wavelength range of 400±10 nm, 440±10 nm, 470±10 nm, or 600 nm to 750 nm, and light in the above-mentioned specific wavelength may have a peak wavelength in a wavelength range of 400±10 nm, 440±10 nm, 470±10 nm, or 600 nm to 750 nm.

Further, light generated by the light source 310 may have a wavelength range of 790 nm to 820 nm or 905 nm to 970 nm, and may have a peak wavelength in a wavelength range of 790 nm to 820 nm or 905 nm to 970 nm.

Further, the light source 310 may comprise a light source that applies excitation light having a peak wavelength in a wavelength range of 390 nm to 470 nm. In this case, an image for medical use (in-vivo image), which includes information about the fluorescence of a fluorescent material present in an object to be examined (living body), can be acquired. A pigment agent for a fluorescence method (Fluorestin, Acridine orange, or the like) may be used to acquire a fluorescence image.

It is preferable that the type (a laser light source, a xenon light source, a light-emitting-diode (LED) light source, and the like) and wavelength of the light source 310, whether or not a filter is present, and the like are determined according to the type of a subject, the purpose of observation, and the like. Further, it is preferable that the wavelengths of illumination light are combined and/or switched according to the type of a subject, the purpose of observation, and the like at the time of observation. In a case where the wavelengths are to be switched, for example, a disc-shaped filter (rotary color filter) provided with filters, which are disposed in front of a light source and transmit or block light having specific wavelengths, may be rotated to switch the wavelength of light to be applied.

Furthermore, an image pick-up element, which is used to embody the invention, is not limited to a color image pick-up element where a color filter is provided for each pixel as with the image pick-up element 134, and may be a monochromatic image pick-up element. In a case where a monochromatic image pick-up element is used, image pick-up can be performed in order of surface (in order of color) while the wavelengths of illumination light (observation light) are sequentially switched. For example, the wavelengths of illumination light to be emitted may be sequentially switched among purple, blue, green, and red; and broadband light (white light) may be applied and the wavelengths of illumination light to be emitted may be switched by the rotary color filter (red, green, blue, purple, and the like). Moreover, one or a plurality of narrow-band lights (green light, blue light, and the like) may be applied and the wavelengths of illumination light to be emitted may be switched by the rotary color filter (green, blue, and the like). The narrow-band lights may be infrared lights (first narrow-band light and second narrow-band light) having two or more different wavelengths. In a case where image pick-up is performed in order of surface (in order of color) in this way, images may be acquired with a change in the intensity of illumination light among the respective colors and may be combined and images of the respective color lights, which are acquired with constant intensity of illumination light among the respective colors, may be superimposed and combined.

The light guide connector 108 (see FIG. 1) is connected to the light source device 300, so that illumination light applied from the light source device 300 is transmitted to the illumination lenses 123A and 123B through the light guide 170 and is applied to an observation range from the illumination lenses 123A and 123B.

Configuration of Processor

The configuration of the processor 200 will be described with reference to FIG. 2. The image signals output from the endoscope 100 are input to the processor 200 through an image input controller 202, and the processor 200 performs necessary image processing on the image signals by an image processing unit 204 (a medical diagnosis support device, a computer) and outputs the image signals to the monitor 400 through a video output unit 206. Accordingly, an observation image (a medical image, a picked-up image), a recognition result thereof, and the like are displayed on the monitor 400 (display device). These kinds of processing are performed under the control of a central processing unit (CPU) 210. That is, the CPU 210 has function as an image processing unit. A communication control unit 205 controls communication with a hospital information system (HIS), a hospital local area network (LAN), and the like. The image of a subject (a medical image, a picked-up image), the detection result of a region of interest, the discrimination result of an image, and the like are recorded in a recording unit 207. A voice processing unit 209 outputs messages (voice) or the like, which correspond to the results of the detection and/or classification of a region of interest, from a speaker 209A by the control of the CPU 210 and the image processing unit 204. Further, the voice processing unit 209 (a medical diagnosis support device, a receiving section) collects user's voice by a microphone 209B, and can recognize which operation (the switching of recognition, the switching of an object to be displayed, or the like) is performed. That is, the voice processing unit 209 and the microphone 209B function as a receiving section that receives a user's operation.

Furthermore, a read only memory (ROM) 211 is a non-volatile storage element (a non-temporary recording medium), and computer-readable codes of a program, which cause the CPU 210 and/or the image processing unit 204 (a medical diagnosis support device, a computer) to perform a medical diagnosis support method according to an embodiment of the invention, are stored in the ROM 211. A random access memory (RAM) 212 is a storage element for temporary storage at the time of various kinds of processing, and can also be used as a buffer at the time of acquisition of an image.

Functions of Image Processing Unit

Figure 4:
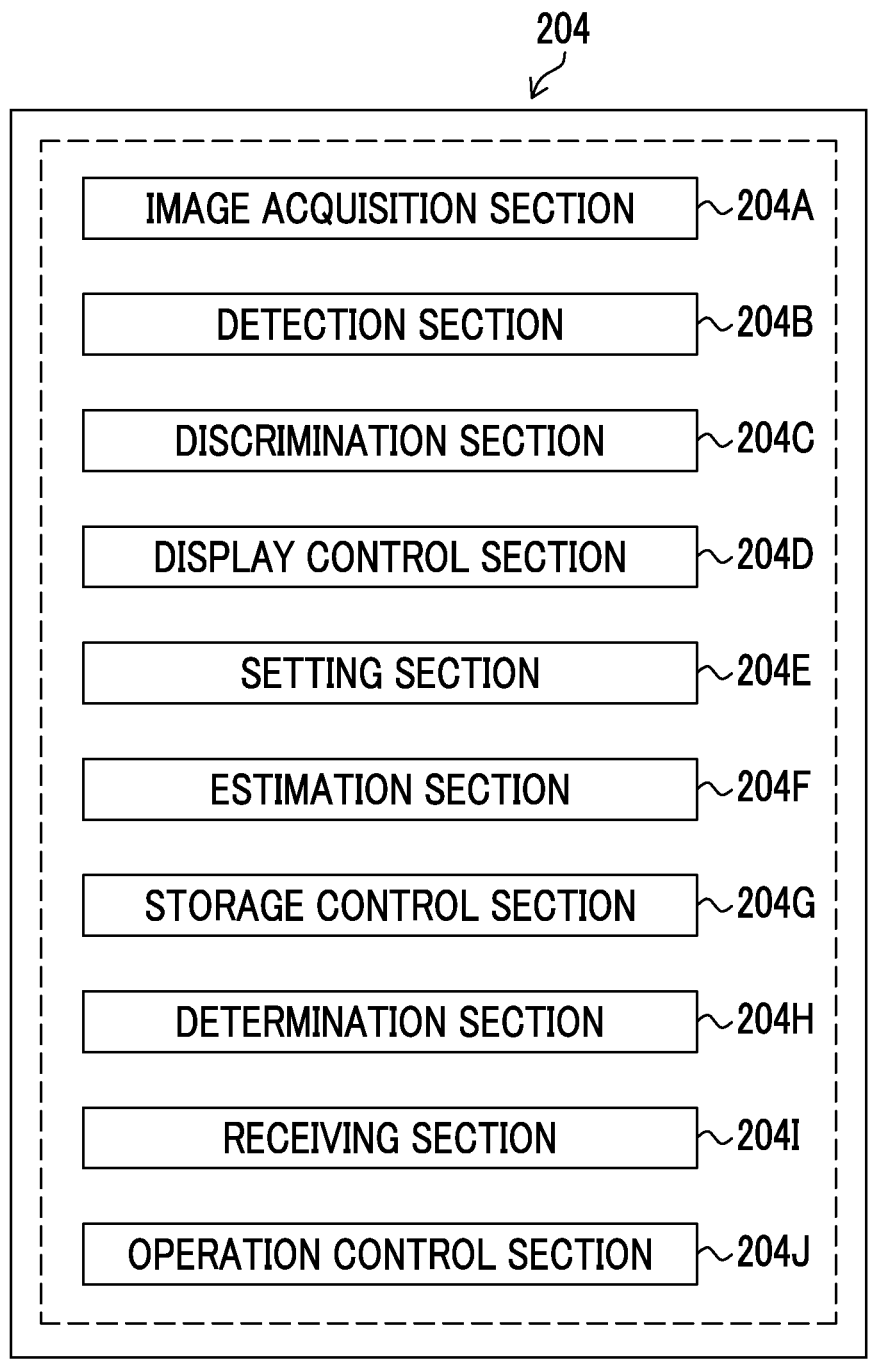
FIG. 4 is a diagram showing the functional configuration of an image processing unit.

FIG. 4 is a diagram showing the functional configuration of the image processing unit 204. The image processing unit 204 includes an image acquisition section 204A (image acquisition section), a detection section 204B (detection section), a discrimination section 204C (discrimination section), a display control section 204D (display control section), a setting section 204E (setting section), an estimation section 204F (estimation section), a storage control section 204G (storage control section), a determination section 204H (determination section), a receiving section 204I (receiving section), and an operation control section 204J (operation control section). The image processing unit 204 also operates as a medical image-analysis processing unit. The image processing unit 204 may comprise a repetition control section that continues processing (detecting, discriminating, and displaying) a medical image until an end condition (an end instruction operation performed by a user, or the like) is satisfied.

The image processing unit 204 may comprise a special-light-image acquisition section that acquires a special light image including information about the specific wavelength range on the basis of a normal light image obtained from the application of light in a white-light wavelength range or light in a plurality of wavelength ranges as the light in a white-light wavelength range. In this case, a signal in the specific wavelength range can be obtained from an arithmetic operation based on color information about RGB (R: red, G: green, and B: blue) or CMY (C: cyan, M: magenta, and Y: yellow) included in the normal light image.

Further, the image processing unit 204 may comprise a feature-quantity-image generation section generating a feature quantity image from an arithmetic operation based on at least one of a normal light image that is obtained from the application of light in a white-light wavelength range or light in a plurality of wavelength ranges as the light in a white-light wavelength range and a special light image that is obtained from the application of light in a specific wavelength range, and may acquire and display a feature quantity image as a medical image (image for medical use). The display control section 204D may have a function of the feature-quantity-image generation section. Furthermore, the image processing unit 204 may comprise a signal processing section that emphasizes a color in a specific wavelength range by signal processing (for example, emphasizes a subtle difference in the color of a mucous membrane by performing the extension and/or contraction of a color in a color space so that a reddish color becomes more red and a whitish color becomes more white).

Configuration about Detection Section and Discrimination Section

Figure 5:
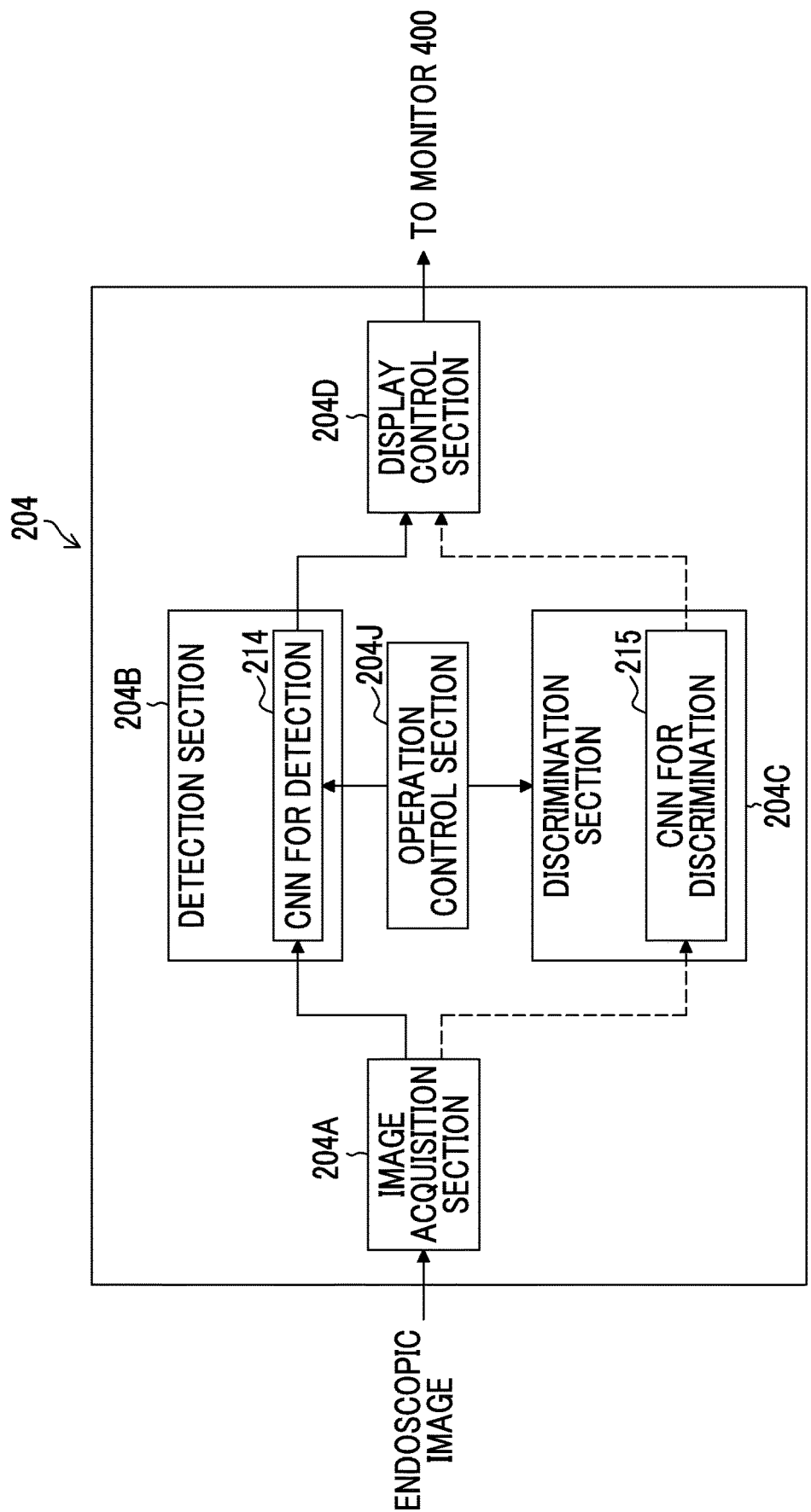
FIG. 5 is a diagram showing the configuration about a detection section and a discrimination section.

FIG. 5 is a diagram mainly showing the configuration about the detection section 204B and the discrimination section 204C of the image processing unit 204. The detection section 204B includes a CNN 214 for detection (first hierarchical network), and the discrimination section 204C includes a CNN 215 for discrimination (second hierarchical network). The CNN 214 for detection and the CNN 215 for discrimination are convolutional neural networks, and have a hierarchical network structure. The CNN 214 for detection is a recognizer that is formed by learning, and detects a region of interest from a medical image. Further, the CNN 215 for discrimination is recognizer that is formed by learning, and performs the discrimination of a medical image. The operation control section 204J (operation control section) operates any one of the detection section 204B (CNN 214 for detection) or the discrimination section 204C (CNN 215 for discrimination). The operation control section 204J may determine whether to operate which of the detection section 204B and the discrimination section 204C according to a user's operation that is given through the operation unit 208 or the like, and may determine whether to operate which of the detection section 204B and the discrimination section 204C regardless of a user's operation. FIG. 5 shows a state where the operation control section 204J operates the detection section 204B and an endoscopic image (medical image) acquired by the image acquisition section 204A is input to the CNN 214 for detection, but the operation control section 204J can also operate the discrimination section 204C to input the endoscopic image to the CNN 215 for discrimination. The flow of processing in this case is shown in FIG. 5 by a dotted line. The image processed by the detection section 204B and the discrimination section 204C, a detection result, and a discrimination result are displayed on the monitor 400 (display device) by the control of the display control section 204D.

Layer Configuration of CNN for Detection and CNN for Discrimination

The layer configuration of the above-mentioned CNNs (the CNN 214 for detection and the CNN 215 for discrimination) will be described. The configuration of the CNN 214 for detection will be described as configuration common to the CNN 214 for detection and the CNN 215 for discrimination, but the same configuration can be employed even in the CNN 215 for discrimination. In an example shown in FIG. 6A, the CNN 214 for detection includes an input layer 214A, an intermediate layer 214B, and an output layer 214C. An endoscopic image (for example, the normal light image) is input to the input layer 214A, and the input layer 214A outputs a feature quantity. The intermediate layer 214B includes convolutional layers 216 and pooling layers 217, the feature quantity output from the input layer 214A is input to the intermediate layer 214B, and the intermediate layer 214B calculates another feature quantity. Since these layers have a structure where a plurality of "nodes" are connected to each other by "edges", these layers include a plurality of weight parameters. The value of the weight parameter is changed with the progress of learning. The layer configuration of the CNN 214 for detection is not limited to a case where one convolutional layer 216 and one pooling layer 217 are repeatedly arranged, and may be a case where either layer (for example, the convolutional layer 216) is successively arranged a plurality of times.

Processing in Intermediate Layer

The intermediate layer 214B calculates a feature quantity by convolution operations and pooling processing. The convolution operation performed in the convolutional layer 216 is processing for acquiring a feature map by a convolution operation using a filter, and plays a role in extracting a feature, such as extracting edges from an image. A "feature map" of one channel is generated from one filter by the convolution operation using the filter. The size of the "feature map" is subjected to downscaling by convolution, and is reduced as convolution is performed in each layer. The pooling processing performed in the pooling layer 217 is processing for reducing (or increasing) the size of the feature map, which is output by the convolution operation, to generate a new feature map, and plays a role in giving robustness to the extracted feature so that the extracted feature is not affected by parallel translation and the like. The intermediate layer 214B can be formed of one or a plurality of layers that perform these kinds of processing.

Among the layers of the intermediate layer 214B, low-order feature extraction (the extraction of edges and the like) is performed in the convolutional layers close to the input side and high-order feature extraction (the extraction of features about the shape, structure, and the like of an object) is performed in the convolutional layers close to the output side. In a case where segmentation is to be performed, upscaling is performed in the convolutional layers positioned in the latter half portion and a "feature map" having the same size as an input image set is obtained in the last convolutional layer. On the other hand, since position information just has to be output in a case where the detection of an object is to be performed, upscaling is not essential.

The intermediate layer 214B may include layers, which perform batch normalization, in addition to the convolutional layers 216 and the pooling layers 217. Batch normalization processing is processing for normalizing the distribution of data by the mini batch in a case where learning is performed, and plays a role in progressing learning fast, lowering dependency on an initial value, suppressing overlearning, and the like.

Processing in Output Layer

In the CNN 214 for detection, the output layer 214C is a layer that detects the position of a region of interest included in an input medical image on the basis of the feature quantity output from the intermediate layer 214B and outputs the result thereof. Since the CNN 214 for detection performs segmentation, the output layer 214C grasps the position of a region of interest appearing in the image with a pixel level by the "feature map" that is obtained from the intermediate layer 214B. That is, the output layer 214C detects whether or not each pixel of the endoscopic image belongs to a region of interest, and can output a detection result. In a case where the detection of an object is to be performed, determination at a pixel level is not necessary and the output layer 214C outputs the position information of an object.

In the CNN 215 for discrimination, the output layer 214C performs the discrimination of the medical image and outputs the result thereof. For example, the output layer 214C may classify an endoscopic image into three categories of "tumor", "non-tumor", and "other"; may output three scores corresponding to "tumor", "non-tumor", and "other" (the sum of three scores is 100%) as a discrimination result; and may output a classification result in a case where the endoscopic image can be clearly classified from three scores. In a case where a discrimination result is to be output as with the CNN 215 for discrimination, it is preferable that an intermediate layer 215B includes an entire bonding layer 218 as one last layer or a plurality of layers (see FIG. 6B). The same configuration as the configuration of the above-mentioned CNN 214 for detection can be used for the other layers.

The CNN 214 for detection having the above-mentioned configuration can be formed by learning (for example, machine learning, such as deep learning) that uses an image and information about the position of a region of interest in the image. Likewise, the CNN 215 for discrimination can be formed by learning that uses an image and information about the category of the image.

Fulfillment of Functions of Image Processing Unit by Processor and the Like

The functions of the above-mentioned image processing unit 204 can be fulfilled using various processors. The various processors include, for example, a central processing unit (CPU) that is a general-purpose processor fulfilling various functions by executing software (program). Further, the above-mentioned various processors also include a graphics processing unit (GPU) that is a processor specialized for image processing, and a programmable logic device (PLD) that is a processor of which circuit configuration can be changed after manufacture, such as a field programmable gate array (FPGA). Furthermore, the above-mentioned various processors also include dedicated electrical circuitry, which is a processor having circuit configuration designed exclusively to perform specific processing, such as an application specific integrated circuit (ASIC).

The functions of each unit may be fulfilled by one processor, or may be fulfilled by a plurality of same kind or different kinds of processors (for example, a plurality of FPGAs, a combination of a CPU and an FPGA, or a combination of a CPU and a GPU). Further, a plurality of functions may be fulfilled by one processor. As an example where a plurality of functions are formed by one processor, first, there is an aspect where one processor is formed of a combination of one or more CPUs and software as typified by a computer, such as an image processing device body or a server, and this processor fulfils a plurality of functions. Second, there is an aspect where a processor fulfilling the functions of the entire system by one integrated circuit (IC) chip as typified by System On Chip (SoC) or the like is used. In this way, various functions are formed using one or more of the above-mentioned various processors as hardware structures. Furthermore, the hardware structures of these various processors are more specifically electrical circuitry where circuit elements, such as semiconductor elements, are combined. These kinds of electrical circuitry may be electrical circuitry fulfilling the above-mentioned functions by using OR, AND, logical NOT, exclusive OR, and a logical operation that is a combination thereof.

In a case where the above-mentioned processor or electrical circuitry is to execute software (program), processor (computer)-readable codes of the software to be executed are stored in a non-temporary recording medium, such as a read only memory (ROM), and the processor refers to the software. The software stored in the non-temporary recording medium includes programs that are used to acquire, detect, and discriminate a medical image and to control the display of a result. The codes may be recorded not in the ROM but in various magneto-optical recording devices or non-temporary recording mediums, such as semiconductor memories. In a case where processing is to be performed using software, for example, a random access memory (RAM) is used as a temporary storage region and the processor or electrical circuitry can also refer to data stored in, for example, an electronically erasable and programmable read only memory (EEPROM) (not shown).

The processing to be fulfilled by these functions of the image processing unit 204 will be described in detail later. The processing to be fulfilled by these functions is performed under the control of the CPU 210.

Configuration of Operation Unit

The processor 200 comprises the operation unit 208 (receiving section). Since the operation unit 208 comprises an illumination light setting switch, a foot switch (not shown), and the like, it is possible to set illumination light to be used (which one of normal light (white light) or special light, such as narrow-band light, is to be used or which wavelength of narrow-band light is to be used in the case of narrow-band light). Further, since the operation unit 208 includes a keyboard and a mouse (not shown), a user can perform an operation for setting an image pick-up condition and a display condition, an operation for setting a waiting time, an operation for setting and switching recognition (detection or discrimination), an operation for setting and switching illumination light, an instruction to pick up (an instruction to acquire) a video or a static image, and the like through these devices (an instruction to pick up a video or a static image may be given by the image pick-up button 144). These operations for setting may be performed through the above-mentioned foot switch and the like; or may be performed by voice (that can be processed by the microphone 209B and the voice processing unit 209), the line of sight, gesture, or the like. That is, the operation unit 208 functions as a receiving section that receives a user's operation.

Configuration of Recording Unit

Since the recording unit 207 (recording device) includes various magneto-optical recording mediums, a non-temporary recording medium, such as a semiconductor memory, and a control section for these recording mediums, an endoscopic image (a medical image or an image for medical use), the detection result of a region of interest, the discrimination result of the medical image, and the like can be recorded in association with each other. The image and the information are displayed on the monitor 400 by an operation, which is performed through the operation unit 208, and the control of the CPU 210 and/or the image processing unit 204.

Configuration of Display Device

The monitor 400 (display device) displays the endoscopic image, the detection result of the region of interest, the discrimination result of the medical image, and the like by the operation, which is performed through the operation unit 208, and the control of the CPU 210 and/or the image processing unit 204. Further, the monitor 400 includes a touch panel (not shown) that is used to perform an operation for setting an image pick-up condition and/or an operation for setting a display condition.

Medical Diagnosis Support Method

Figure 7:
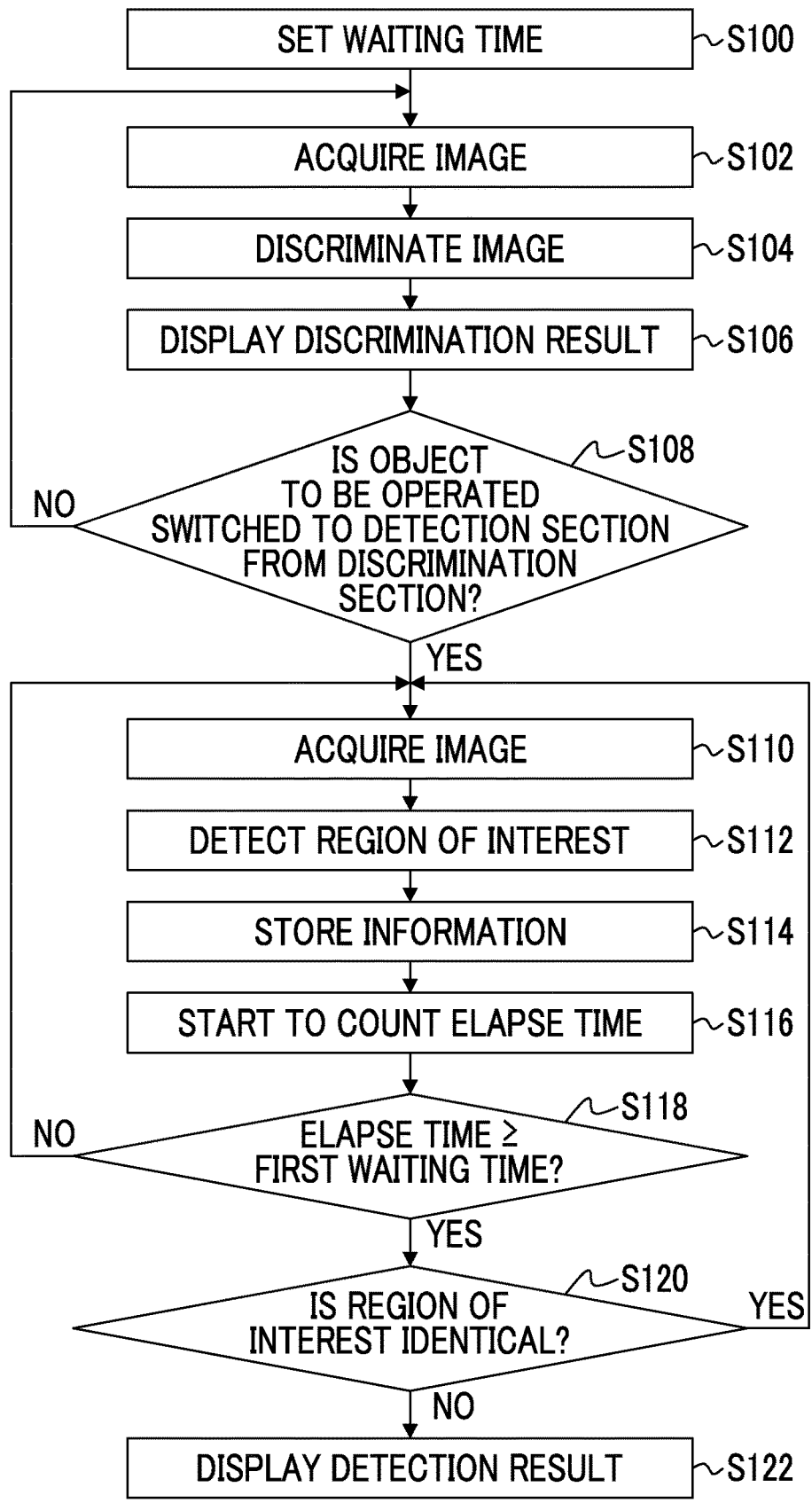
FIG. 7 is a flowchart showing a procedure of a medical diagnosis support method according to the first embodiment.

A medical diagnosis support method using the endoscope system 10 having the above-mentioned configuration will be described. FIG. 7 is a flowchart showing a procedure of the medical diagnosis support method according to the first embodiment. FIG. 7 shows processing in a case where an object to be displayed is a discrimination result in an initial state and is switched to a detection result thereafter.

Setting of Waiting Time

Figure 8:
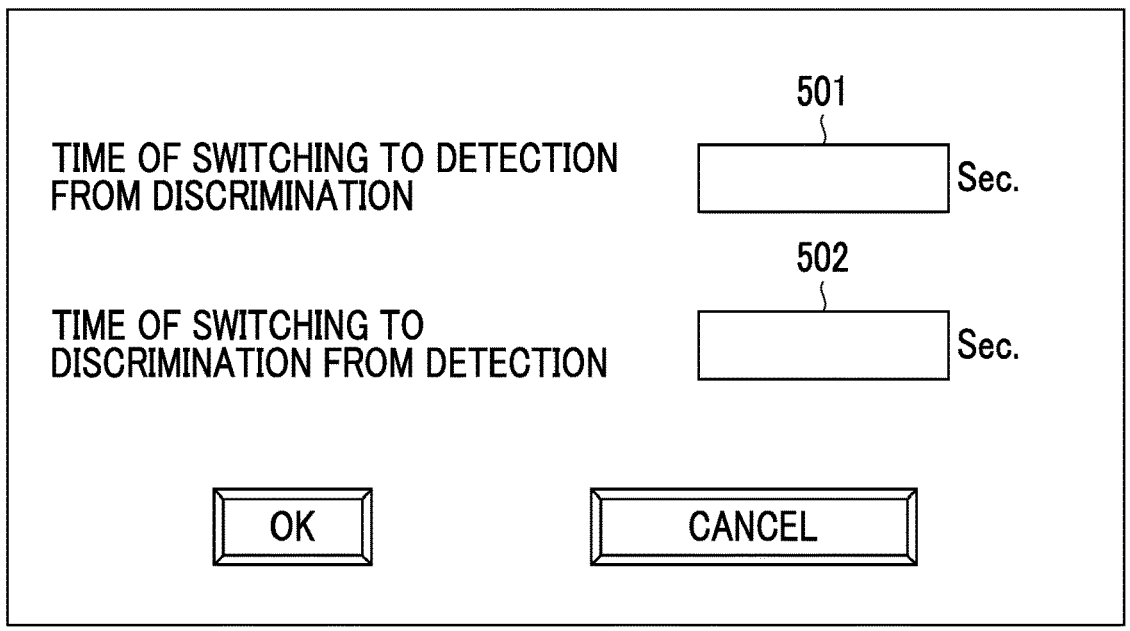
FIG. 8 is a diagram showing an example of a setting screen for a waiting time.

The setting section 204E (setting section) sets waiting times for the display of a recognition result (Step S100: waiting time-setting step). The setting section 204E can set waiting times on the basis of a user's operation that is received by the operation unit 208 (receiving section). For example, as shown in FIG. 8, a user can input a waiting time (first waiting time), which is required in a case where an object to be displayed is switched to a result of detection from a result of discrimination, to a region 501 of a waiting time setting screen displayed on the monitor 400, and can input a waiting time (second waiting time), which is required in a case where an object to be displayed is switched to a result of discrimination from a result of detection, to a region 502. The setting section 204E may set the first waiting time and the second waiting time to different values (the same applies to an example to be described below).

Figure 9:
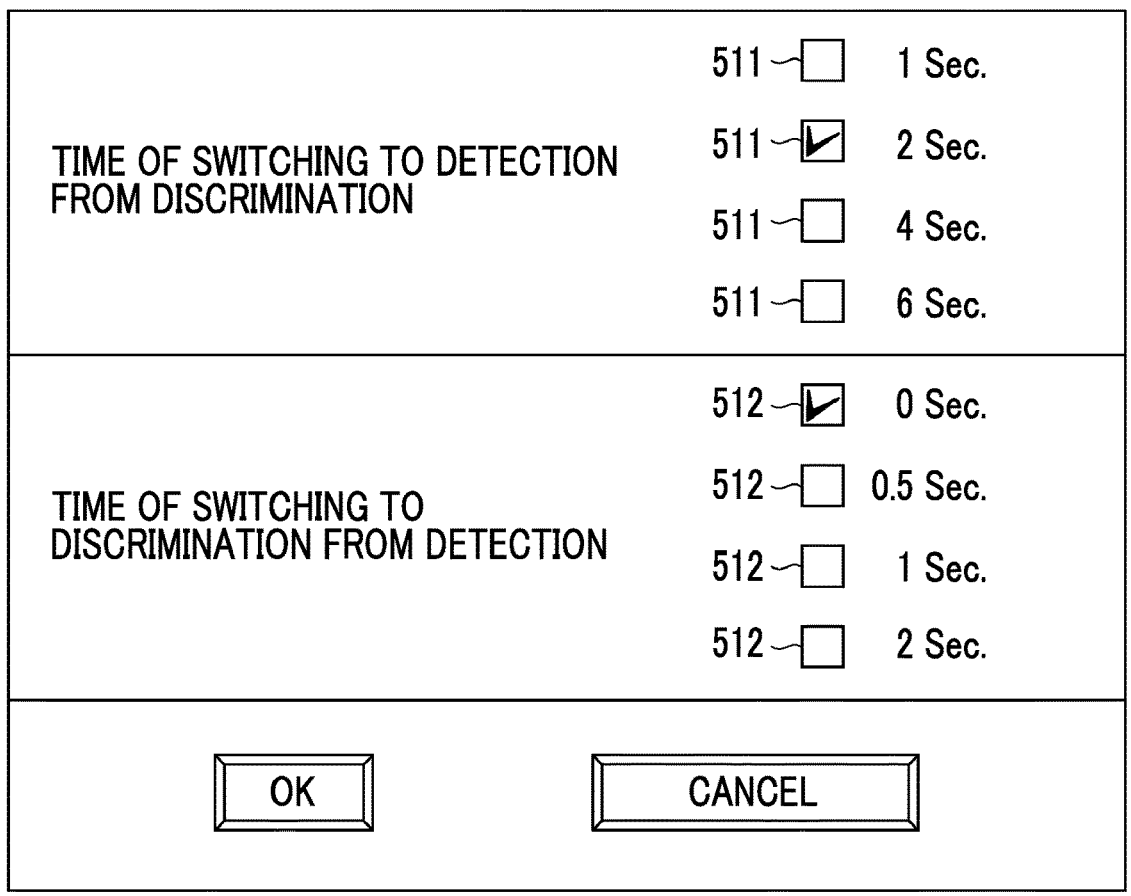
FIG. 9 is a diagram showing another example of a setting screen for a waiting time.

The setting section 204E may set waiting times, which are selected from a plurality of predetermined waiting times by a user's operation, as the waiting times. For example, as shown in FIG. 9, a user can select the first waiting time by checking a checkbox 511 of the waiting time setting screen displayed on the monitor 400 and can select the second waiting time by checking a checkbox 512.

The setting section 204E can also set the first waiting time and the second waiting time on the basis of the amount of movement between frames of medical images. In this case, the estimation section 204F (estimation section) can estimate the amount of movement on the basis of a difference between the frames or the like and the setting section 204E can set the waiting times according to the estimated amount of movement. Specifically, for example, in a case where the amount of movement is larger than a threshold value, the setting section 204E sets a waiting time, which is shorter than a waiting time corresponding to the threshold value, as the waiting time. In a case where the amount of movement is equal to or smaller than the threshold value, the setting section 204E sets a waiting time, which is longer than a waiting time corresponding to the threshold value, as the waiting time. The reason why a waiting time is set in this way is to shorten a waiting time since a different subject (a region of interest or the like) is likely to be seen in a case where the amount of movement is large (movement is fast) and to lengthen a waiting time since the same subject is likely to be seen in a case where the amount of movement is small (movement is slow) (In this case, there is a concern that diagnosis may be hindered since a user feels inconvenient in a case where a result is instantly displayed). A plurality of threshold values and a plurality of waiting times corresponding to the threshold values may be set.

Figure 10:
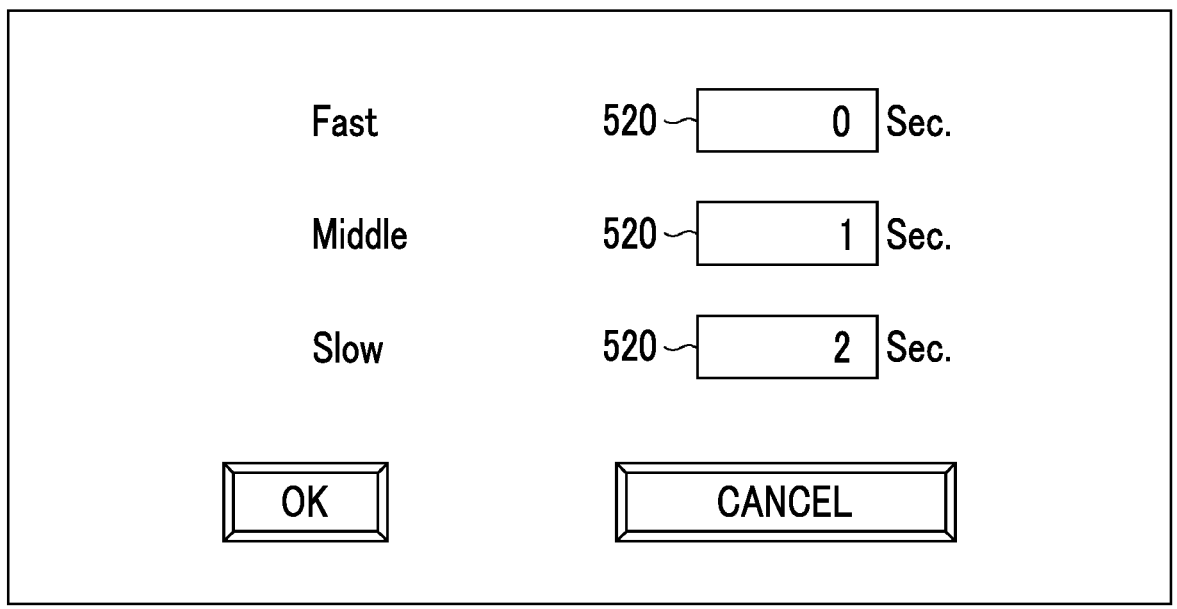
FIG. 10 is a diagram showing an example of a setting screen for a waiting time corresponding to the amount of movement.

FIG. 10 is a diagram showing an aspect where a waiting time corresponding to the amount of movement is set on the basis of a user's operation. A user can input waiting times, which are required in the case of "Fast" (movement is fast, that is, the amount of movement is large), in the case of "Middle" (movement is medium, that is, the amount of movement is medium), and in the case of "Slow" (movement is slow, that is, the amount of movement is small), to regions 520 of a waiting time setting screen displayed on the monitor 400. With regard to the setting of a waiting time, the amount of movement may be divided into two stages (for example, "fast" and "slow") or may be finely divided into three or more stages. Such a setting can be performed in the same way at the first waiting time and the second waiting time. The setting section 204E may set waiting times while using a specific amount of movement, for example, the amount of movement required in the case of "Middle" as the above-mentioned threshold value. In a case where the estimated amount of movement is larger than the threshold value, the setting section 204E can determine this case as the case of "Fast" and can set a waiting time that is shorter than a waiting time corresponding to "Middle". In a case where the estimated amount of movement is smaller than the threshold value, the setting section 204E can determine this case as the case of "Slow" and can set a waiting time that is longer than a waiting time corresponding to "Middle".

Since there is a case where the contents of recognition and illumination light correspond to each other, such as a case where the detection of a region of interest is performed with normal light (white light) and discrimination is performed with special light (narrow-band light or the like), a waiting time may be set according to illumination light to be used. Further, in a case where illumination light is switched from normal light to special light used for detection of Linked Color Imaging (LCI: registered trademark) or the like, the same lesion or the same region of interest is likely to be observed before and after the switching. Accordingly, it is preferable that a waiting time is set to zero to continuously display notification information (recognition result). As in the case of the amount of movement, the setting of a waiting time according to illumination light may also be performed according to a user's operation or may also be performed regardless of a user's operation.

A user (a doctor or the like) can easily set a desired waiting time by this kind of setting of a waiting time. The setting of a waiting time can be frequently performed not only at the time of start of processing but also after the start of processing. Further, conditions, such as illumination light and an image pick-up condition, other than the waiting times may be set in Step S100.

Acquisition of Medical Image

In Step S102, the light source device 300 applies illumination light on the basis of the setting (the setting and switching of illumination light) that is performed through the operation unit 208 and the like, the images (the endoscopic images or the medical images) of an object to be examined are picked up by the image pick-up optical system 130, and the image acquisition section 204A acquires the picked-up images (image acquisition step). The image acquisition section 204A can acquire a plurality of medical images in time series with a determined frame rate. In a case where the discrimination of the medical images is to be performed, for example, special light (an example of second bright light), such as blue narrow-band light, can be used as illumination light but other illumination light may be used.

Recognition (Discrimination) of Medical Image

The operation control section 204J inputs the acquired medical images to the discrimination section 204C (CNN 215 for discrimination), and the discrimination section 204C discriminates (classifies) the medical images by the CNN 215 for discrimination (Step S104: discrimination step). Discrimination can be performed for all or some of the medical images, and a user (a doctor or the like) determines whether or not a target region is benign or malignant on the basis of the result thereof. In a case where a region of interest has been detected, discrimination may be performed for the region of interest. The discrimination section 204C may determine which range is to be discriminated on the basis of a user's operation that is performed through the operation unit 208, or may determine which range is to be discriminated regardless of a user's operation. Examples of discrimination can include the type of a lesion (a hyperplastic polyp, an adenoma, an intramucosal carcinoma, an invasive carcinoma, or the like), the range of a lesion, the size of a lesion, the visual shape of a lesion, the stage diagnosis of a cancer, the current position in a lumen (the pharynx, the esophagus, the stomach, the duodenum, or the like as an upper portion; and the appendix, the ascending colon, the transverse colon, the descending colon, the sigmoid colon, the rectum, or the like as a lower portion), and the like.

Figure 11A:
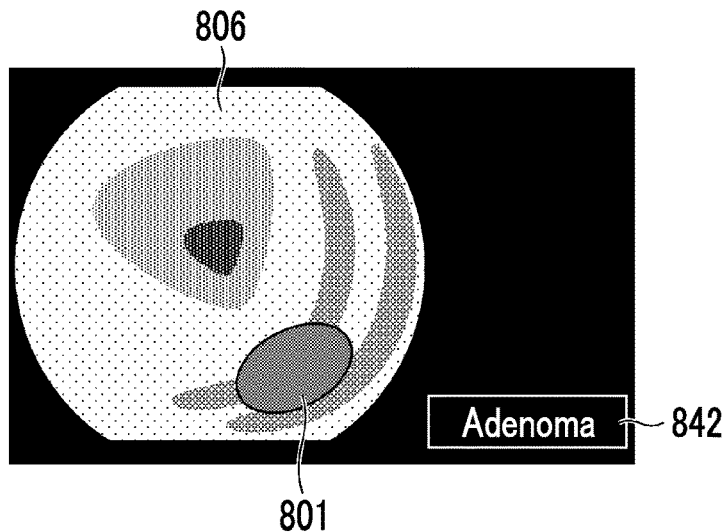
FIGS. 11A, 11B, and 11C are diagrams showing the display examples of a discrimination result.
Figure 11B:
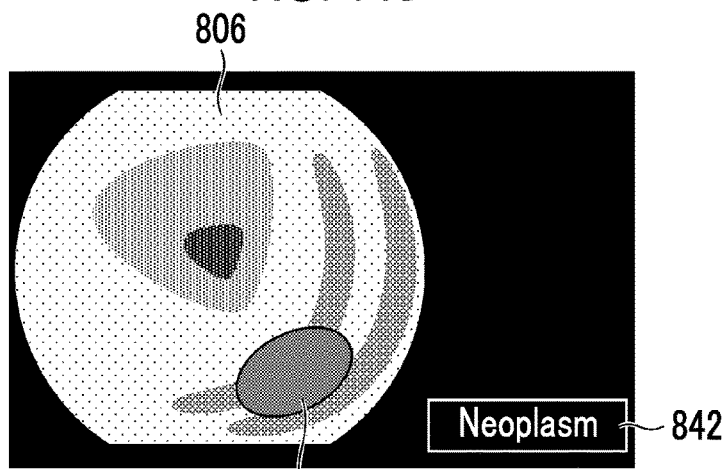
Figure 11C:
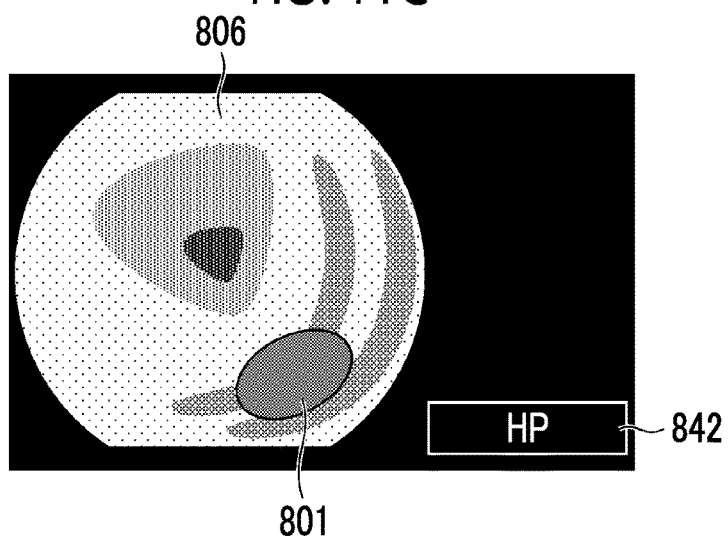

The display control section 204D causes the monitor 400 (display device) to display a result according to this result of discrimination (Step S106: display control step). Since an object to be displayed is in the initial state (discrimination) without being switched at the time of Step S106, the result may be displayed instantly (with a waiting time of zero). FIGS. 11A, 11B, and 11C are diagrams showing examples of the display of a result, and the discrimination result of a medical image 806 is displayed in a region 842 (each of FIGS. 11A, 11B, and 11C show a state where a region 801 of interest is included). FIGS. 11A, 11B, and 11C show examples of cases where a discrimination result is an adenoma, a neoplasm (tumor), and a hyperplastic polyp (HP). The display control section 204D may display information (that can be calculated by the CNN 215 for discrimination), which represents the reliability of a discrimination result, by a numerical value, a figure (for example, bar display), a symbol, a color, or the like. Further, the discrimination section 204C may notify a user of information, which represents a discrimination result, through the voice processing unit 209 and the speaker 209A with voice (the same applies to the detection section 204B).

Recognition (Detection) of Medical Image

The operation control section 204J operates the discrimination section 204C until an object to be operated is switched to the detection section from the discrimination section (while NO in Step S108), and the display control section 204D causes the result thereof to be displayed. In a case where an object to be operated is switched to the detection section from the discrimination section (YES in Step S108), the operation control section 204J operates the detection section 204B to input the medical images to the CNN 214 for detection (Step S110: image acquisition step). The light source device 300 may switch illumination light while interlocking with the switching of an object to be operated (for example, switching to white light at detection from blue narrow-band light at discrimination), or may maintain illumination light (may switch illumination light independently of the switching of an object to be operated) until a user's switching operation is performed.

Detection of Region of Interest

The CNN 214 for detection (first hierarchical network) performs the above-mentioned segmentation, so that the detection section 204B detects a region of interest included in the medical images (Step S112: detection step). Examples of the region of interest (region of concern) detected in Step S112 can include a polyp, a cancer, the colonic diverticula, an inflammation, treatment scars (an endoscopic mucosal resection (EMR), an endoscopic submucosal dissection (ESD), a clipped portion, and the like), a bleeding point, a perforation, blood vessel heteromorphism, and the like. The detection section 204B may detect a region of interest by means other than a CNN. For example, the detection section 204B may detect a region of interest on the basis of the feature quantity of pixels of an acquired medical image. In this case, the detection section 204B divides a target image to be detected into, for example, a plurality of rectangular regions; sets each of the plurality of divided rectangular regions as a local region; calculates the feature quantity (for example, hue) of pixels in every local region of the target image to be detected; and determines a local region, which has specific hue, among the respective local regions as the region of interest. Likewise, the discrimination section 204C may also perform discrimination on the basis of a feature quantity.

Display of Detection Result

Figure 12:
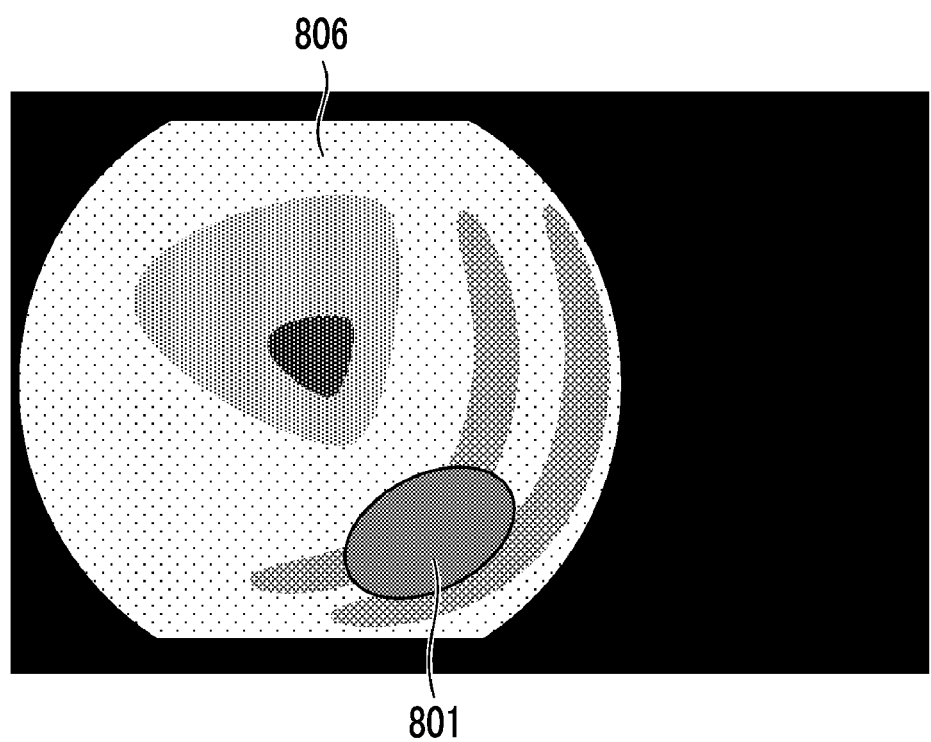
FIG. 12 is a diagram showing an example of a screen until a waiting period has passed.
Figure 14:
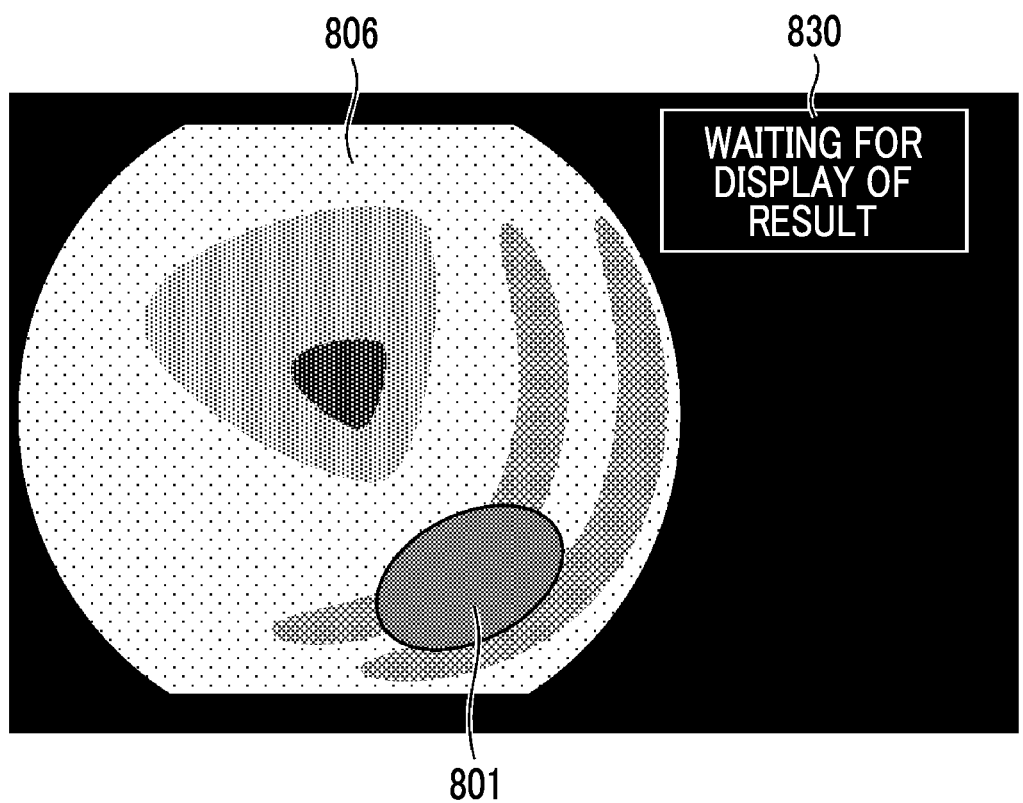
FIG. 14 is a diagram showing the display example of information showing a state where a result is not displayed.

In a case where an object to be operated is switched between the detection section and the discrimination section, the display control section 204D determines that an object to be displayed is switched between a result of detection and a result of discrimination and causes a result of detection, which is obtained from an operation, to be displayed. However, when the waiting time (first waiting time) has passed after detection is performed and in a case where the region of interest is a region of interest having been already detected, the display control section 204D does not display a result as described below. Until the recognition result is displayed, the display control section 204D causes the monitor 400 to display the acquired medical image 806 without a recognition result as shown in FIG. 12. Until the waiting time has passed, the display control section 204D may cause the monitor 400 (display device) to display information representing that a result of detection is not displayed in addition to the medical image (in an example of FIG. 14, a message of "waiting for the display of a result" is displayed in a region 830). In a case where a result is not displayed, there is a possibility that a user is anxious about whether or not the device operates correctly. However, in a case where the information is displayed as described above, such an anxiety can be eliminated. Whether or not to display the information may be determined according to a user's operation that is performed through the operation unit 208.

In a case where detection is performed, the storage control section 204G stores information (for example, feature quantities, such as a shape and a size) about the region of interest, which is detected from the medical image, in the recording unit 207 (storage device) (Step S114: storage control step). As described later, the identity of the region of interest is determined on the basis of this information. The display control section 204D starts to count elapse time after the region of interest is detected (Step S116: display control step), but processing of Steps S110 to S114 is repeated without the display of a result of detection until the first waiting time has passed (while NO in Step S118). In a case where the first waiting time has passed (YES in Step S118), the determination section 204H determines whether or not the region of interest detected by the detection section is a region of interest having been already detected on the basis of the information stored in Step S114 (Step S120: determination step). As a result, in a case where it is determined that "the region of interest detected by the detection section is identical to a region of interest having been already detected" (YES in Step S120), the display control section 204D does not display a detection result and processing returns to Step S110. Accordingly, it is possible to prevent a user feeling inconvenient due to the repeated display of the result of the region of interest having been already detected. In a case where the waiting time is set to a time sufficiently longer than an observation time for the region of interest, a case where a result is not displayed practically can be also included in a case where "a result is not displayed".

Figure 13A:
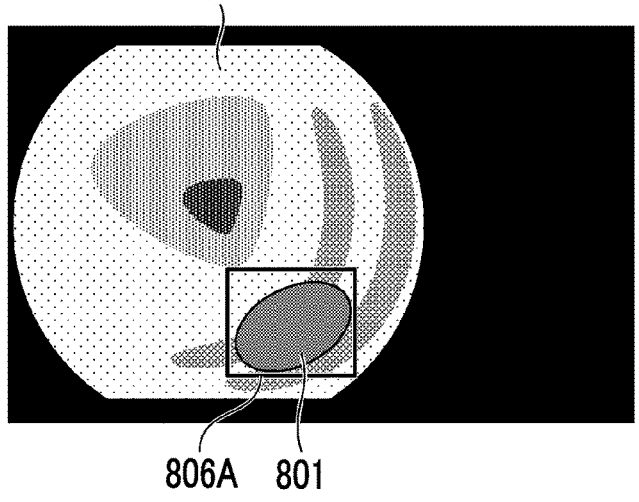
FIGS. 13A, 13B, and 13C are diagrams showing the display examples of a detection result.
Figure 13B:
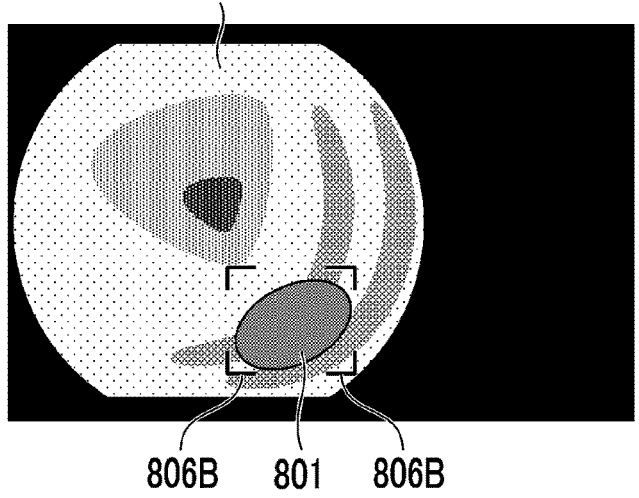
Figure 13C:
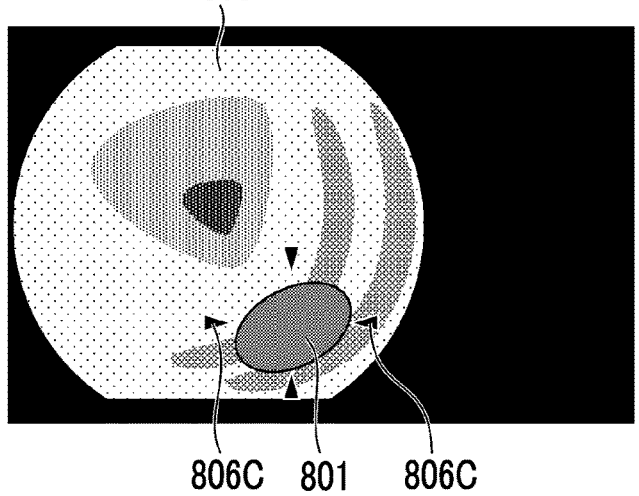

In a case where the determination of Step S120 is negative (in a case where the region of interest detected by the detection section is a new region of interest), the display control section 204D causes the monitor 400 (display device) to display a detection result after the lapse of the first waiting time (Step S120: display control step). FIGS. 13A, 13B, and 13C are diagrams showing the display examples of a detection result, and a frame 806A surrounding the region 801 of interest, a marker 806B, and a marker 806C (examples of information representing a position where the region of interest is detected) are displayed on the region 801 of interest included in the medical image 806 as shown in FIGS. 13A, 13B, and 13C, respectively. The display control section 204D may notify a user of information, which represents the detection result of the region of interest, through the voice processing unit 209 and the speaker 209A with voice. After the display or notification of a detection result, processing returns to Step S110 and detection may continue to be performed or processing returns to Step S102 and discrimination may be performed.

In a case where an object to be displayed is switched to a result of detection from a result of discrimination, as described above, the result of detection is displayed when the waiting time (first waiting time) has passed after detection is performed. Accordingly, since a recognition result about the same subject (a region of interest or the like) is not displayed immediately after switching, a user does not feel inconvenient and observation or diagnosis is not hindered. As a result, the visibility of a recognition result of a medical image is high.

Figure 15:
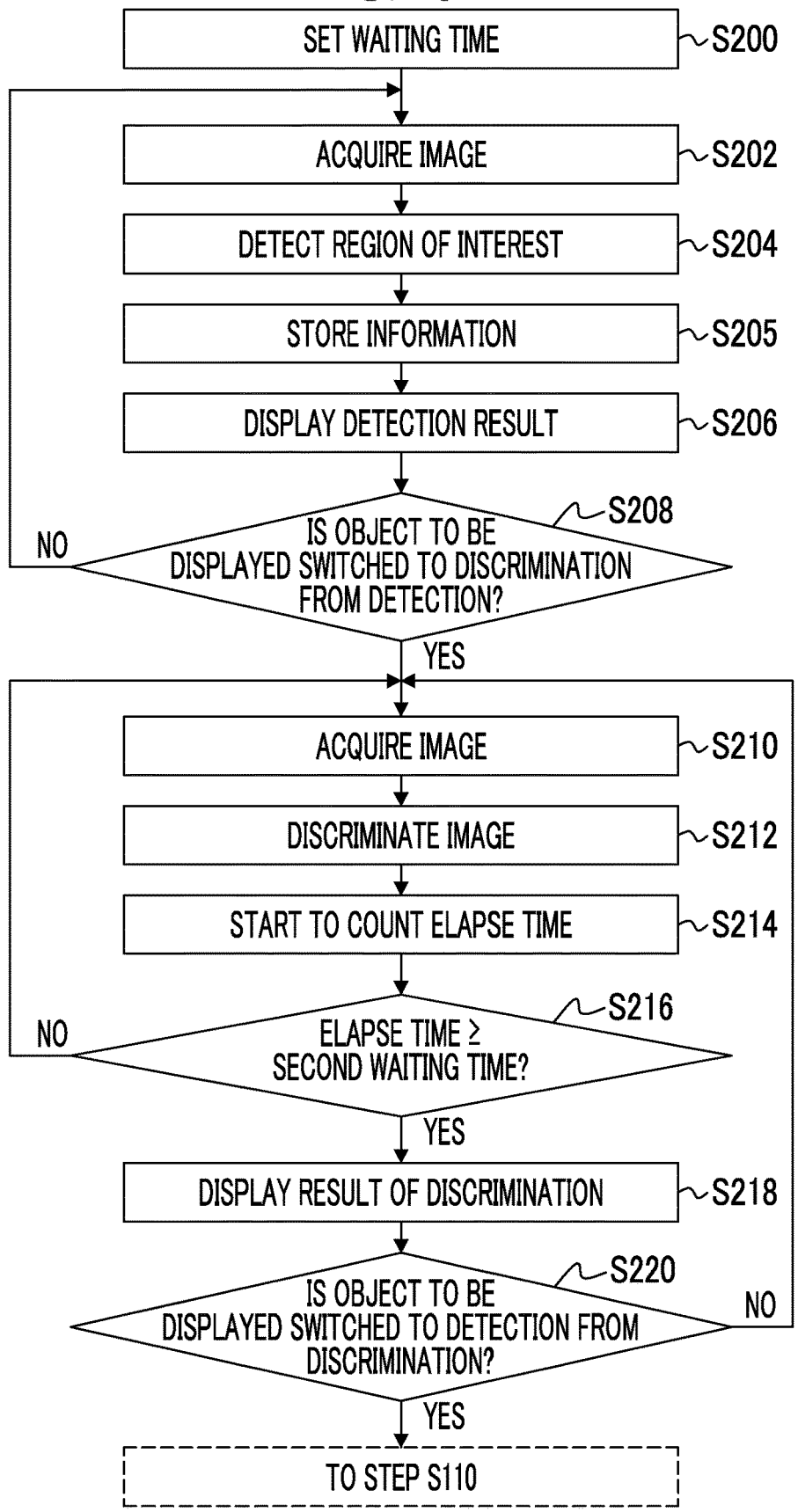
FIG. 15 is another flowchart showing a procedure of the medical diagnosis support method according to the first embodiment.

Case where Object to be Displayed is Switched to Result of Discrimination from Result of Detection Display in a case where an object to be displayed is switched to a result of discrimination from a result of detection will be described with reference to a flowchart of FIG. 15. In this case, conditions, such as waiting times, are set as in the above-mentioned step S100 (Step S200: setting step), and the acquisition of an image, the detection of a region of interest, the control of storage, and the display of a detection result are performed in Steps S202 to S206 (an image acquisition step, a detection step, a storage control step, and a display control step) as in Steps S110 to S114 and S122. As in the case of the flowchart of FIG. 7, the light source device 300 may switch illumination light while interlocking with the switching of an object to be operated (for example, switching to blue narrow-band light at discrimination from white light at detection), or may maintain illumination light until a user's switching operation is performed. Until an object to be displayed is switched to a result of discrimination from a result of detection (while NO in Step S208), these kinds of processing are repeated. After an object to be displayed is switched to a discrimination result from a detection result, processing proceeds to Step S210. The acquisition and discrimination of a medical image are performed in Steps S210 and S212 (the image acquisition step and a discrimination step) as in Steps S102 and S104, and elapse time starts to be counted after the discrimination is performed (Step S214: display control step). Processing of Steps S210 to S214 is repeated until the second waiting time has passed (while NO in Step S216), and the display control section 204D causes the monitor 400 to display a discrimination result as shown in FIGS. 11A, 11B, and 11C when the second waiting time has passed (Step S218: display control step). As described above, the second waiting time may be the same as the first waiting time, or may be different from the first waiting time (may be zero). Until an object to be operated and an object to be displayed are switched to detection (while NO in Step S220), processing of Steps S210 to S214 is repeated. After an object to be operated and an object to be displayed are switched to detection, processing proceeds as in Step S110 of FIG. 7 and Steps subsequent to Step S110.

In a case where an object to be displayed is switched to a result of discrimination from a result of detection, as described above, the result of discrimination is displayed when the waiting time (second waiting time) has passed after discrimination is performed. Accordingly, since a recognition result about the same subject (a region of interest or the like) is not displayed immediately after switching, a user does not feel inconvenient and observation or diagnosis is not hindered. As a result, the visibility of a recognition result of a medical image is high. Display shown in FIG. 14 may be performed until the second waiting time has passed.

In a case where a found lesion is to be discriminated for the first time, or the like, there is also a case where it is preferable that a discrimination result is instantly displayed without a waiting time even though display is switched for the same lesion to discrimination from detection. In this case, a discrimination result can be displayed instantly in a case where the waiting time (second waiting time) is set to zero in Step S200. As described above in Steps S114 and S120, the storage control section 204G can store information about the region of interest in the recording unit 207 and the determination section 204H can determine whether or not the lesion is an identical lesion on the basis of the information.

Modification Example of Configuration about Detection and Discrimination

Figure 16:
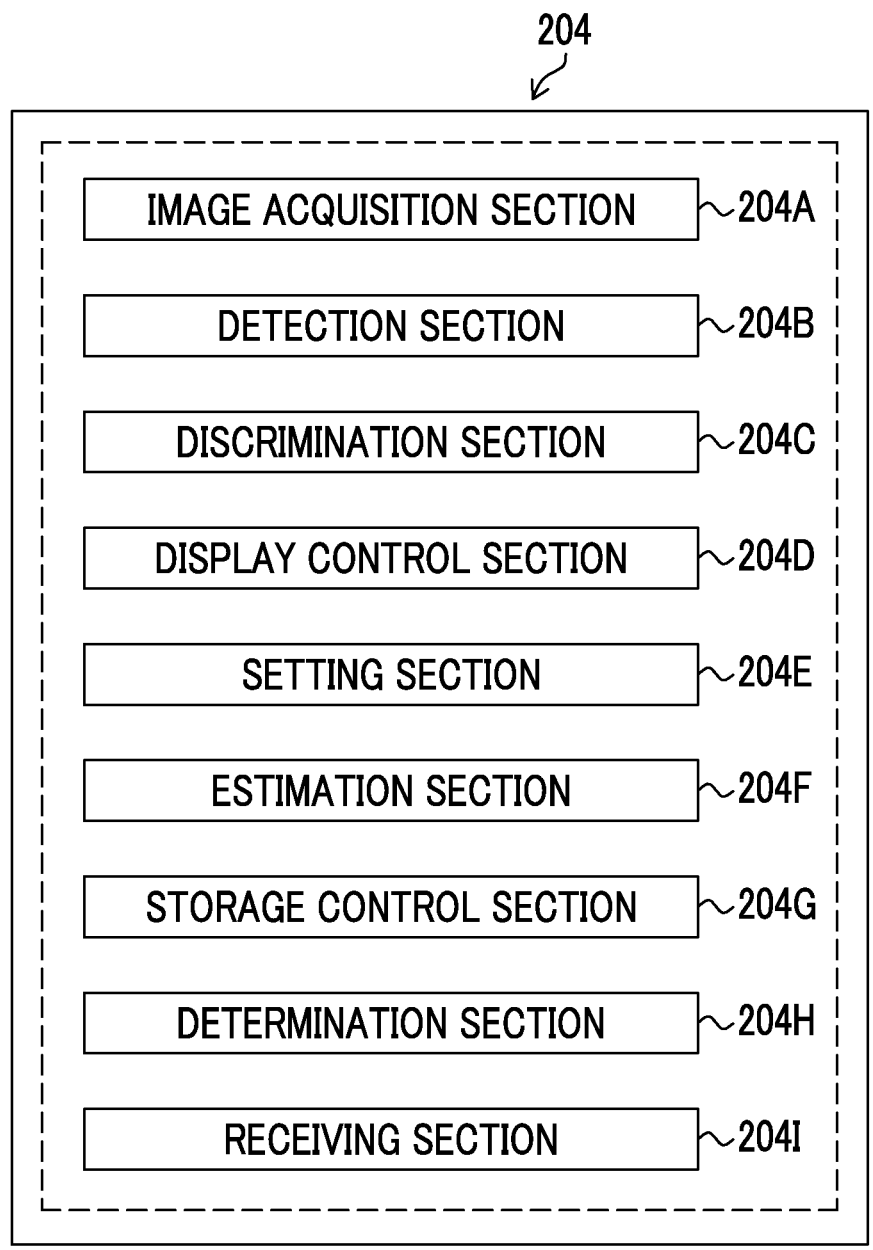
FIG. 16 is a diagram showing another example of the functional configuration of the image processing unit.
Figure 17:
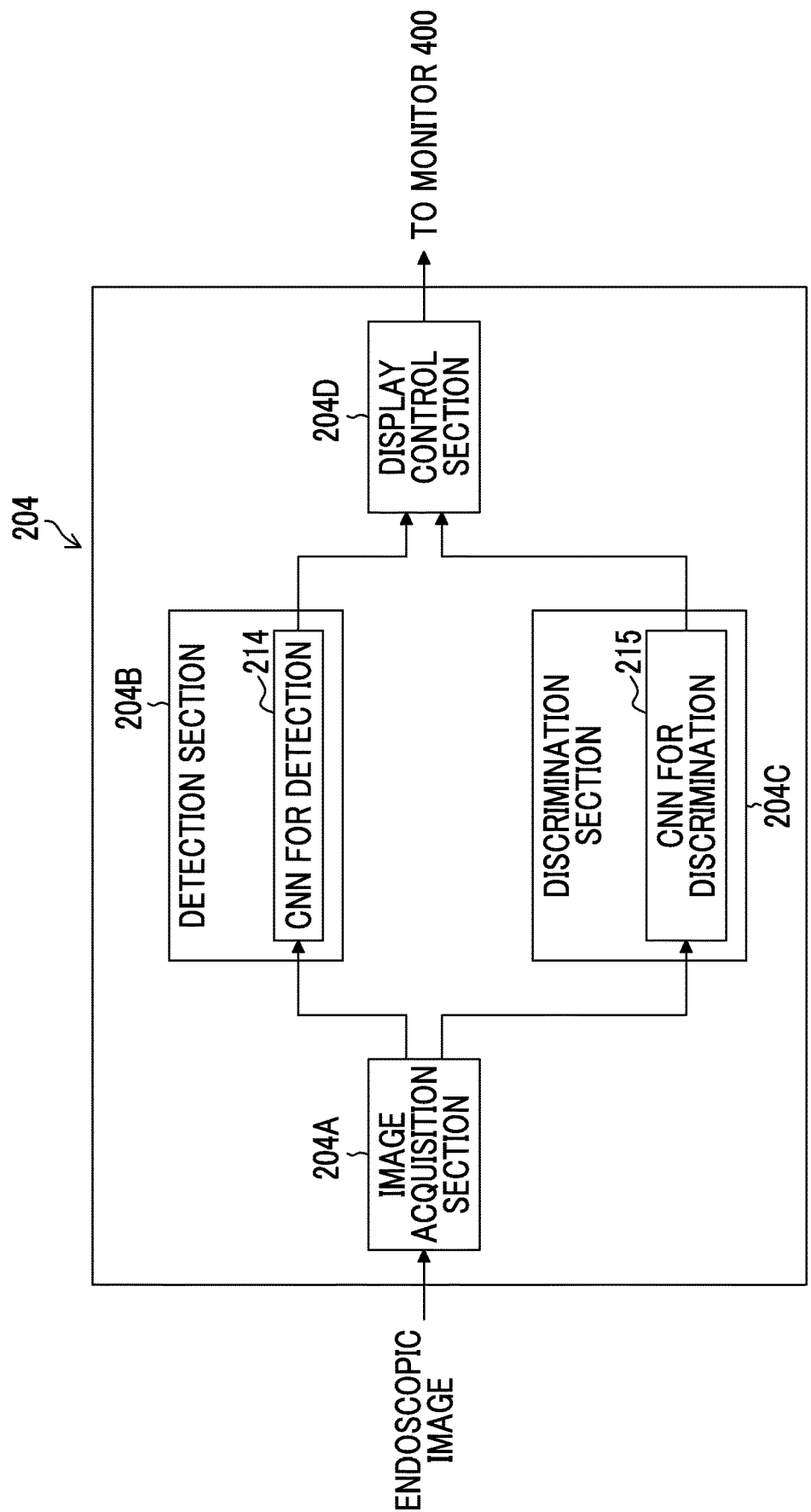
FIG. 17 is a diagram showing a modification example of the configuration about the detection section and the discrimination section.

In the medical diagnosis support device and the medical diagnosis support method according to the embodiment of the invention, detection performed by the detection section and discrimination performed by the discrimination section may be performed in parallel and a result of detection or a result of discrimination may be displayed by the switching of an object to be displayed. FIG. 16 is a functional block diagram of an image processing unit 204 of a modification example of this configuration about detection and discrimination. In this configuration, the operation control section 204J is excluded from the configuration shown in FIG. 4. Further, FIG. 17 is a diagram showing configuration about the detection section 204B and the discrimination section 204C, and shows a state where medical images acquired by the image acquisition section 204A are input to both the detection section 204B and the discrimination section 204C. Other configuration of the endoscope system 10 is the same as the configuration described above with reference to FIGS. 1 to 3 and the like. "Performed in parallel" includes a case where both detection and discrimination are performed for frames of the medical images acquired in time series.

Figure 18:
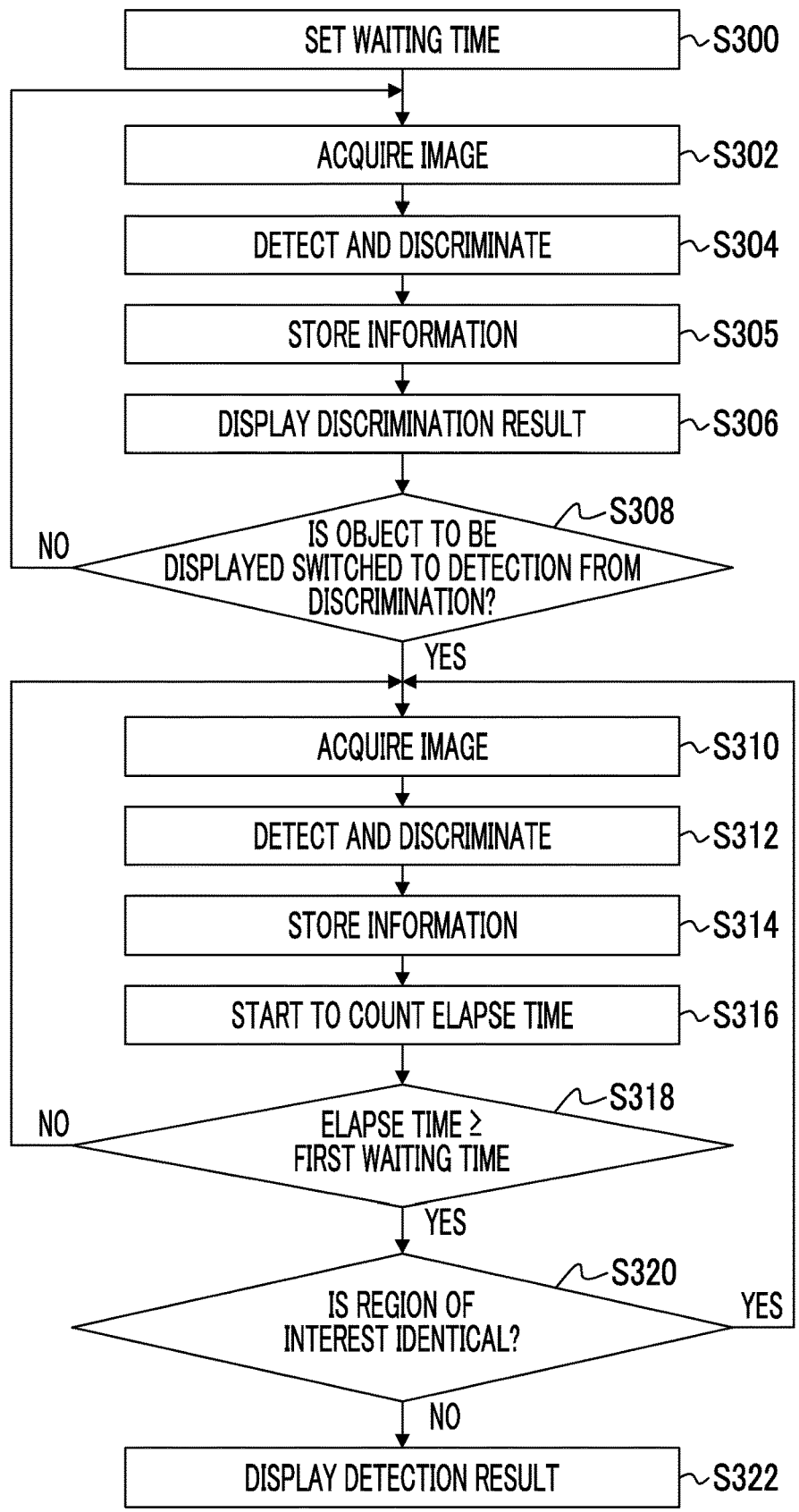
FIG. 18 is a flowchart showing a procedure of a medical diagnosis support method according to the modification example.

FIG. 18 is a flowchart showing of a medical diagnosis support method according to the modification example, and shows processing in a case where an object to be displayed is switched to detection from discrimination (initial state) (corresponding to FIG. 7). In the flowchart of FIG. 18, processing of Steps S300 and S302 (a setting step and an image acquisition step) is the same as the processing of Steps S100 and S102, respectively. In Step S304, detection and discrimination are performed by the detection section 204B and the discrimination section 204C (a detection step and a discrimination step). Information about a detected region of interest is stored in the recording unit 207 (storage device) (Step S305: storage control step). The display of a discrimination result in Step S306 (display control step) can be performed as in Step S106 (see FIGS. 11A, 11B, and 11C). These kinds of processing continue to be performed until an object to be displayed is switched to a result of detection from a result of discrimination (while NO in Step S308).

In a case where an object to be displayed is switched to a result of detection from a result of discrimination, the same processing as the processing of Steps S302 to S305 is performed in Steps S310 to S314 (an image acquisition step, a discrimination step, a detection step, and a storage control step) and the display control section 204D starts to count elapse time (Step S316: display control step). In a case where elapse time reaches the first waiting time (YES in Step S318) and the detected region of interest is not identical to a region of interest having been already detected (NO in Step S320), the display control section 204D causes the monitor 400 to display a detection result as in FIG. 13 (Step S322: display control step). The display of information shown in FIG. 14 may be performed until the first waiting time has passed. Further, after a detection result is displayed, detection may continue to be performed or processing may return to discrimination. In a case where an object to be displayed is switched to discrimination from detection and is then switched to detection again (the same case as FIG. 15), a detection result is displayed when the second waiting time has passed after detection caused by switching performed again is performed.

Even in the modification example of this configuration about detection and discrimination, since a recognition result about the same subject (a region of interest or the like) is not displayed immediately after the switching of an object to be displayed, a user does not feel inconvenient and observation or diagnosis is not hindered. As a result, the visibility of a recognition result of a medical image is high.

Post Processing of Recognition and Display

An aspect where the pick-up, recognition, and display of an image for medical use are performed in parallel (in real time) has been described in the above-mentioned embodiment. However, in the endoscope system 10, an image, which is picked up and recorded in advance, can also be processed (recognized, displayed, and the like) after the fact. For example, the endoscope system 10 can recognize and display the respective frames of endoscopic images (medical images acquired in time series) recorded in the recording unit 207 and can improve the visibility of a recognition result of the medical image even in this post processing. The post processing of recognition and display may be performed by a device (a device independent of the endoscope system 10), such as a processor, or a computer that does not comprise image pick-up parts (an endoscope, a light source device, an image pick-up unit, and the like).

Additional Remarks

Configuration to be described below is also included in the scope of the invention in addition to the first embodiment and the modification example having been described above.

Additional Remark 1

A medical image processing device comprising:

a medical image-analysis processing unit that detects a region of interest, which is a region to be noticed, on the basis of the feature quantity of pixels of a medical image; and a medical image-analysis result acquisition unit that acquires an analysis result of the medical image-analysis processing unit.

Additional Remark 2

A medical image processing device comprising:

a medical image-analysis processing unit that detects whether or not an object to be noticed is present on the basis of the feature quantity of pixels of a medical image; and a medical image-analysis result acquisition unit that acquires an analysis result of the medical image-analysis processing unit.

Additional Remark 3

The medical image processing device, wherein the medical image-analysis result acquisition unit acquires the analysis result from a recording device recording an analysis result of the medical image, and the analysis result includes any one or both of the region of interest that is the region to be noticed included in the medical image and whether or not the object to be noticed is present.

Additional Remark 4

The medical image processing device, wherein the medical image is a normal light image that is obtained from the application of light in a white-light wavelength range or light in a plurality of wavelength ranges as the light in a white-light wavelength range.

Additional Remark 5

The medical image processing device, wherein the medical image is an image that is obtained from the application of light in a specific wavelength range, and the specific wavelength range is a range narrower than the white-light wavelength range.

Additional Remark 6

The medical image processing device, wherein the specific wavelength range is a blue-light wavelength range or a green-light wavelength range of a visible-light wavelength range.

Additional Remark 7

The medical image processing device, wherein the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

Additional Remark 8

The medical image processing device, wherein the specific wavelength range is a red-light wavelength range of a visible-light wavelength range.

Additional Remark 9

The medical image processing device, wherein the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

Additional Remark 10

The medical image processing device, wherein the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin.

Additional Remark 11

The medical image processing device, wherein the specific wavelength range includes a wavelength range of $400\pm10$ nm, $440\pm10$ nm, $470\pm10$ nm, or 600 nm to 750 nm, and light in the specific wavelength range has a peak wavelength in a wavelength range of $400\pm10$ nm, $440\pm10$ nm, $470\pm10$ nm, or 600 nm to 750 nm.

Additional Remark 12

The medical image processing device, wherein the medical image is an in-vivo image of the inside of a living body, and the in-vivo image includes information about the fluorescence of a fluorescent material present in the living body.

Additional Remark 13

The medical image processing device, wherein the fluorescence is obtained from the application of excitation light, which has a peak wavelength in a wavelength range of 390 nm to 470 nm, to the inside of the living body.

Additional Remark 14

The medical image processing device, wherein the medical image is an in-vivo image of the inside of a living body, and the specific wavelength range is an infrared wavelength range.

Additional Remark 15

The medical image processing device, wherein the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

Additional Remark 16

The medical image processing device, wherein a medical image acquisition unit comprises a special-light-image acquisition section that acquires a special light image including information about the specific wavelength range on the basis of a normal light image obtained from the application of light in a white-light wavelength range or light in a plurality of wavelength ranges as the light in a white-light wavelength range, and the medical image is the special light image.

Additional Remark 17

The medical image processing device, wherein a signal in the specific wavelength range is obtained from an arithmetic operation based on color information about RGB or CMY included in the normal light image.

Additional Remark 18

The medical image processing device further comprising:

a feature-quantity-image generation section generating a feature quantity image from an arithmetic operation based on at least one of the normal light image that is obtained from the application of light in a white-light wavelength range or light in a plurality of wavelength ranges as the light in a white-light wavelength range and the special light image that is obtained from the application of light in a specific wavelength range, the medical image is the feature quantity image.

Additional Remark 19

An endoscope apparatus comprising:

the medical image processing device according to any one of Additional remarks 1 to 18; and an endoscope that acquires an image from the application of at least one of light in a white-light wavelength range or light in the specific wavelength range.

Additional Remark 20

A diagnosis support apparatus comprising:

the medical image processing device according to any one of Additional remarks 1 to 18.

Additional Remark 21

A medical service support apparatus comprising:

the medical image processing device according to any one of Additional remarks 1 to 18.

The embodiment and other aspects of the invention have been described above, but the invention is not limited to the above-mentioned aspects and can have various modifications without departing from the scope of the invention.

EXPLANATION OF REFERENCES

10: endoscope system
100: endoscope
102: hand operation part
104: insertion part
106: universal cable
108: light guide connector
112: soft portion
114: bendable portion
116: hard distal end portion
116A: distal end-side end face
123: illumination unit
123A: illumination lens
123B: illumination lens
126: forceps port
130: image pick-up optical system
132: image pick-up lens
134: image pick-up element
136: drive circuit
138: AFE
141: air/water supply button
142: suction button
143: function button
144: image pick-up button
170: light guide
200: processor
202: image input controller
204: image processing unit
204A: image acquisition section
204B: detection section
204C: discrimination section
204D: display control section
204E: setting section
204F: estimation section
204G: storage control section
204H: determination section
204I: receiving section
204J: operation control section
205: communication control unit
206: video output unit
207: recording unit
208: operation unit
209: voice processing unit
209A: speaker
209B: microphone
210: CPU
211: ROM
212: RAM
214: CNN for detection
215: CNN for discrimination
214A: input layer
214B: intermediate layer
214C: output layer
215B: intermediate layer
216: convolutional layer
217: pooling layer
218: entire bonding layer
300: light source device
310: light source
310B: blue light source
310G: green light source
310R: red light source
310V: purple light source
330: stop
340: condenser lens
350: light source control unit
400: monitor
501: region
502: region
511: checkbox
512: checkbox
520: region
801: region of interest
806: medical image
806A: frame
806B: marker
806C: marker
830: region
842: region
S100 to S322: respective steps of medical diagnosis support method

What is claimed is:

1. An endoscope system comprising:

a monitor;

an endoscope configured to be inserted into an object;

a light source configured to apply one of first illumination light and second illumination light different from the first illumination light to the object; and one or more processors configured to:

acquire medical images picked-up through the endoscope in time series, the medical images including a first image picked-up with the first illumination light and a second image picked-up with the second illumination light;
   detect a lesion appearing in the first image;
   discriminate a type of a lesion appearing in the second image;
   and
   display, on the monitor, a result of the detection in a case in which the first illumination light is applied to the object; and
   display, on the monitor, a result of the discrimination in a case in which the second illumination light is applied to the object,
   wherein a switching between the first illumination light and the second illumination light and a switching between the detection and the discrimination are interlocked; and
the second illumination light includes a peak wavelength in a range of 390 nm to 450 nm.

2. The endoscope system according to claim 1, wherein the type of the lesion to be discriminated includes a tumor and a non-tumor.

3. The endoscope system according to claim 1, wherein the type of the lesion to be discriminated includes at least one of an adenoma or an invasive carcinoma.

4. The endoscope system according to claim 1, wherein:
   a wavelength range of the second illumination light is narrower than a wavelength range of the first illumination light.

5. The endoscope system according to claim 1, wherein:
   the second illumination light further includes a peak wavelength in a wavelength range of 530 nm to 550 nm.

6. The endoscope system according to claim 1, wherein the one or more processors are configured to display the result of the detection along with the first image.

7. The endoscope system according to claim 1, wherein the one or more processors are configured to display the result of the discrimination along with the second image on the monitor.

8. The endoscope system according to claim 1, wherein the one or more processors are configured to display the result of the detection on the monitor in a case in which a first waiting time has passed after switching from performing the discrimination to performing the detection.

9. The endoscope system according to claim 1, wherein the one or more processors are configured to display the result of the discrimination on the monitor in a case in which a second waiting time has passed after switching from performing the detection to performing the discrimination.

10. The endoscope system according to claim 1, wherein the one or more processors are configured to:
   display the result of the detection on the monitor in a case in which a first waiting time has passed after switching from performing the discrimination to performing the detection; and
   display the result of the discrimination on the monitor in a case in which a second waiting time has passed after switching from performing the detection to performing the discrimination,
   wherein the second waiting time is different from the first waiting time.

11. The endoscope system according to claim 1, further comprising a switch configured to receive a user's operation, wherein the one or more processors are configured to:
   receive the user's operation through the switch; and
   according to the received user's operation, switch the display between displaying the result of the detection and displaying the result of the discrimination.

12. The endoscope system according to claim 11, wherein the one or more processors are configured to display the result of the detection on the monitor in a case in which a first waiting time has passed after receiving the user's operation to switch the display from displaying the result of the discrimination to displaying the result of the detection.

13. The endoscope system according to claim 11, wherein the one or more processors are configured to control the display to display the result of the discrimination on the monitor in a case in which a second waiting time has passed after receiving the user's operation to switch the display from displaying the result of the detection to displaying the result of the discrimination.

14. The endoscope system according to claim 1, wherein the one or more processors are configured to:
   perform the detection by using a first hierarchical network; and
   perform the discrimination by using a second hierarchical network.

15. The endoscope system according to claim 1, wherein the one or more processors are configured to superimpose information indicating a position of the lesion on one of the medical images in displaying the result of the detection.

16. The endoscope system according to claim 15, wherein the one or more processors are configured to display information indicating the type of the lesion through characters, numbers, figures, symbols, or colors in displaying the result of the discrimination.

17. The endoscope system according to claim 16, wherein the one or more processors are configured to display the information indicating the type of the lesion in an area different from where the medical images are displayed.

18. The endoscope system according to claim 1, wherein the one or more processors are configured to discriminate the type of the lesion appearing in the second image on which an extension and/or contraction of a color in a color space is performed so that a difference in the color of a mucous membrane is emphasized.

19. A medical diagnosis support method performed with an endoscope system, wherein the endoscope system comprises:
   a monitor;
   an endoscope configured to be inserted into an object; and
   a light source configured to apply one of first illumination light and second illumination light different from the first illumination light to the object,
   the medical diagnosis support method comprising:
   acquiring medical images picked-up through the endoscope in time series, the medical images including a first image picked-up with the first illumination light and a second image picked-up with the second illumination light;
   detecting a lesion appearing in the first image;
   discriminating a type of a lesion appearing in the second image; and
   displaying, on the monitor, a result of the detection in a case in which the first illumination light is applied to the object, and displaying, on the monitor, a result of the discrimination in a case in which the second illumination light is applied to the object,
   wherein a switching between the first illumination light and the second illumination light and a switching between the detection and the discrimination are interlocked, and the second illumination light includes a peak wavelength in a range of 390 nm to 450 nm.

20. The method according to claim 19, wherein a wavelength range of the second illumination light is narrower than a wavelength range of the first illumination light.

21. The method according to claim 19, wherein the step of displaying the result of the detection includes superimposing information indicating a position of the lesion on one of the medical images.

22. The method according to claim 21, wherein the step of displaying the result of the discrimination includes displaying information indicating the type of the lesion as characters, numbers, figures, symbols, or colors.

23. The method according to claim 22, wherein the step of displaying the result of the discrimination includes displaying the information indicating the type of the lesion in an area different from where the medical images are displayed.

* * * * *